(12) United States Patent
Hur

(10) Patent No.: US 9,750,583 B2
(45) Date of Patent: Sep. 5, 2017

(54) FIXTURE REMOVER FOR IMPLANT

(71) Applicants: Ducksu Hur, Seongnam-si, Gyeonggi-do (KR); Jun Song, Bayside, NY (US)

(72) Inventor: Ducksu Hur, Seongnam-si (KR)

(73) Assignees: Ducksu Hur, Seongnam-si (KR); Jun Song, Bayside, NY (US)

( * ) Notice: Subject to any disclaimer, the term of this patent is extended or adjusted under 35 U.S.C. 154(b) by 255 days.

(21) Appl. No.: 14/487,900

(22) Filed: Sep. 16, 2014

(65) Prior Publication Data
US 2016/0067016 A1    Mar. 10, 2016

(30) Foreign Application Priority Data

Sep. 4, 2014  (KR) .......................... 10-2014-0117567

(51) Int. Cl.
*A61C 3/00* (2006.01)
*A61C 3/02* (2006.01)
*A61C 8/00* (2006.01)

(52) U.S. Cl.
CPC .......... *A61C 8/0089* (2013.01); *A61C 8/0022* (2013.01); *A61C 8/0068* (2013.01); *A61C 8/0069* (2013.01)

(58) Field of Classification Search
CPC . A61C 8/0022–8/0025; A61C 8/0068–8/0072; A61C 8/0089–8/0092
USPC ....... 433/141, 145, 152, 146, 147, 153, 161, 433/165
See application file for complete search history.

(56) References Cited

U.S. PATENT DOCUMENTS

| | | | | |
|---|---|---|---|---|
| 4,995,810 A * | 2/1991 | Soderberg | ............ | A61C 8/0089 433/141 |
| 5,073,111 A * | 12/1991 | Daftary | .................. | A61C 8/005 433/173 |
| 5,106,300 A * | 4/1992 | Voitik | .................. | A61C 8/0048 433/173 |
| 5,944,525 A * | 8/1999 | Ura | ....................... | A61C 8/0089 433/141 |
| 5,951,287 A * | 9/1999 | Hawkinson | ............ | A61C 8/005 433/141 |
| 6,068,480 A * | 5/2000 | Misch | .................. | A61C 8/0001 433/173 |

(Continued)

FOREIGN PATENT DOCUMENTS

| | | |
|---|---|---|
| EP | 2283792 A2 | 2/2011 |
| KR | 10-2010-0129669 A | 12/2010 |

(Continued)

*Primary Examiner* — Sundhara Ganesan
*Assistant Examiner* — Garrett Atkinson
(74) *Attorney, Agent, or Firm* — Birch, Stewart, Kolasch & Birch, LLP

(57) ABSTRACT

Disclosed is an implant fixture remover. The fixture remover includes a remover screw which has a first thread formed on one side thereof to be screwed to a female screw portion of an implant fixture implanted into an alveolar bone, and a second thread formed on the other side thereof; and a remover driver including a torque transmitting portion which is slide-inserted into the remover screw, and a torque providing portion which is separated from the torque transmitting portion and screwed to the second thread so that the torque transmitting portion maintains contact with the fixture.

13 Claims, 31 Drawing Sheets

(56) References Cited

U.S. PATENT DOCUMENTS

| | | | | |
|---|---|---|---|---|
| 6,083,004 A * | 7/2000 | Misch | A61C 8/0022 433/173 |
| 6,454,567 B1 * | 9/2002 | Carchidi | A61C 8/0089 433/141 |
| 6,923,648 B1 * | 8/2005 | Rassoli | A61C 8/0087 433/173 |
| 7,137,816 B2 * | 11/2006 | Gervais | A61C 8/0001 433/173 |
| 7,160,109 B2 * | 1/2007 | Gervais | A61C 8/0001 433/141 |
| 7,338,286 B2 * | 3/2008 | Porter | A61C 8/0001 433/172 |
| 7,632,095 B2 * | 12/2009 | Ostman | A61C 5/08 433/172 |
| 8,226,410 B2 * | 7/2012 | Kim | A61C 1/084 433/174 |
| 8,523,568 B2 * | 9/2013 | Heo | A61C 8/0018 433/174 |
| 8,902,355 B2 * | 12/2014 | Dudkowski | H04N 5/2222 348/373 |
| 8,936,467 B2 * | 1/2015 | Anitua Aldecoa | A61C 8/0089 433/152 |
| 8,967,999 B2 * | 3/2015 | Suttin | A61C 1/084 433/72 |
| 2006/0008763 A1 * | 1/2006 | Brajnovic | A61C 8/0089 433/76 |
| 2010/0216094 A1 * | 8/2010 | Ikeya | A61C 8/0025 433/174 |
| 2010/0304329 A1 * | 12/2010 | Heo | A61C 8/0089 433/146 |
| 2011/0306008 A1 * | 12/2011 | Suttin | A61C 1/084 433/72 |
| 2016/0081765 A1 * | 3/2016 | Sanders | A61C 1/084 433/75 |

FOREIGN PATENT DOCUMENTS

| | | |
|---|---|---|
| KR | 10-2011-0033215 A | 3/2011 |
| KR | 10-2012-0002896 A | 1/2012 |

* cited by examiner

FIXTURE REMOVER FOR IMPLANT

CROSS-REFERENCE TO RELATED APPLICATION

This application claims priority to and the benefit of Korean Patent Application No. 10-2014-0117567, filed on Sep. 4, 2014, the disclosure of which is incorporated herein by reference in its entirety.

BACKGROUND

1. Field of the Invention

The present invention relates to an implant fixture remover, and more particularly, to an implant fixture remover to safely and rapidly extract a fixture implanted into an alveolar bone.

2. Discussion of Related Art

Generally, an implant denotes a transplant, an insert, or an artificial device made to replace a lost biological tissue or to serve as the tissue.

A dental implant functions to recover the original function of a tooth by implanting an artificial dental root formed of an alloy such as titanium or the like, to which a human body does not show any adverse reaction, into an alveolar bone from which the tooth is pulled out instead of a dental root of a lost tooth, fusing the artificial dental root to the alveolar bone, and fixing an artificial tooth thereto. In other words, the dental implant denotes a substitute of a lost natural tooth, or denotes a dental treatment of recovering the original function of a tooth by fastening a screwed fixture to an alveolar bone, fusing the fixture to the bone for about 3 to 8 months, and then fixing an abutment as a bonding portion and a prosthesis such as an artificial tooth crown thereto.

The implant treatment is roughly divided into a soft tissue incision and removal operation, a bone removing operation, an implant operation, and an upper prosthesis forming operation. The soft tissue incision and removal operation is substantially similar to a principle of a general operation. The bone removing operation is a process of removing cortical bone and removing cancellous bone. In the process, basically, the bone to be subjected to the fixture is trimmed, a fixture site is marked, a small hole is formed in the alveolar bone and sequentially widened up to a diameter slightly smaller than the diameter of an implant to be implanted, and then the implant is implanted thereto.

On the other hand, in the process of implanting a fixture, a fixture connector may be damaged due to an excessive torque, and thus, may not be inserted or pulled out any more. A fixture inserted into a human bone and successfully fused to the bone may not be maintained any more due to the loss of the bone around the implant resulting from an inflammation caused around the implant over a period of time. In these cases, the fixture has to be removed or separated from the human bone. A removing torque necessary to unscrew the implant fused to the bone is about 100 to 500 Ncm. In the past, since a tool for removing the fixture with such a magnitude of torque was not provided, the bone around the fixture was greatly destroyed and then the fixture was separated and removed.

However, when the bone around the fixture was cut out and the fixture was removed in this way, a fixture could not be re-implanted due to the great loss of the bone or another bone transplanting operation had to be performed to reconstruct the destroyed bone. Accordingly, the operation was made to be greatly complex, thus causing inconvenience to a patient and prolonging the treatment time.

SUMMARY OF THE INVENTION

The present invention is directed to an implant fixture remover which may rapidly and simply extract a fixture from an alveolar bone while minimizing the loss of the alveolar bone.

Further, the present invention is directed to an implant fixture remover which may increase the safety of treatment by safely removing a fixture without cutting out the surrounding alveolar bone and may greatly reduce time for the treatment, when a fixture connection portion is damaged due to an excessive torque in the process of implanting the fixture and may not be inserted or pulled out any more.

According to an aspect of the present invention, there is provided an implant fixture remover including a remover screw which has a first thread formed on one side thereof to be screwed to a female screw portion of an implant fixture implanted into an alveolar bone, and a second thread formed on the other side thereof; and a remover driver including a torque transmitting portion which is slide-inserted into the remover screw, and a torque providing portion which is separated from the torque transmitting portion and screwed to the second thread so that the torque transmitting portion maintains contact with the fixture, wherein a force, which is applied to facing surfaces of the torque providing portion and the torque transmitting portion by a torque generated by turning the torque providing portion after the torque providing portion is screwed to the second thread, is transmitted to the fixture through the torque transmitting portion and works as a repulsive force so that the fixture is extracted from the alveolar bone, and the torque transmitting portion is pressurized toward the fixture.

In an embodiment, a degree of slide insertion of the torque transmitting portion into the remover screw may be determined based on a degree of screw coupling of the torque providing portion and the second thread.

In an embodiment, an implant fixture remover may further include a connection portion connecting the torque transmitting portion to the torque providing portion so that the torque providing portion is screwed to the second thread, while the torque transmitting portion and the torque providing portion coact.

In an embodiment, the connection portion may allow the facing surfaces to be in contact with each other each other before the torque providing portion is screwed to the second thread.

In an embodiment, each of the torque providing portion and the torque transmitting portion may include a first concavity and a second concavity recessed in a circumferential direction, and may further include a first elastic ring and a second elastic ring which are respectively inserted into the first concavity and the second concavity and elastically deformed by contacting the connection portion so that the torque providing portion and the torque transmitting portion are temporarily fixed to coact.

In an embodiment, a direction of the first thread may be formed to be opposite a direction of the second thread.

In an embodiment, the facing surfaces may be defined by at least two normal vectors.

In an embodiment, the facing surfaces may be symmetrically formed based on a virtual plane including a central axis.

In an embodiment, the facing surfaces may include a first facing surface having a first slope based on the central axis, a second facing surface formed continuously with the first facing surface and having a second slope greater than the first slope, and a third facing surface formed continuously with the second facing surface and having a third slope greater than the second slope.

In an embodiment, the third facing surface may be perpendicular to the virtual plane including the central axis.

In an embodiment, the first facing surface, the second facing surface, and the third facing surface may be each provided in a plural number and formed spaced apart from each other.

In an embodiment, the number of the third facing surfaces may be smaller than that of the first facing surface and the second facing surface.

In an embodiment, the facing surfaces of the torque providing portion and the torque transmitting portion may be formed corresponding to each other.

In an embodiment, the torque transmitting portion may include a concave-convex contact surface in contact with the fixture so that a pressure applied toward the fixture, which is generated by the torque providing portion, is increased.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
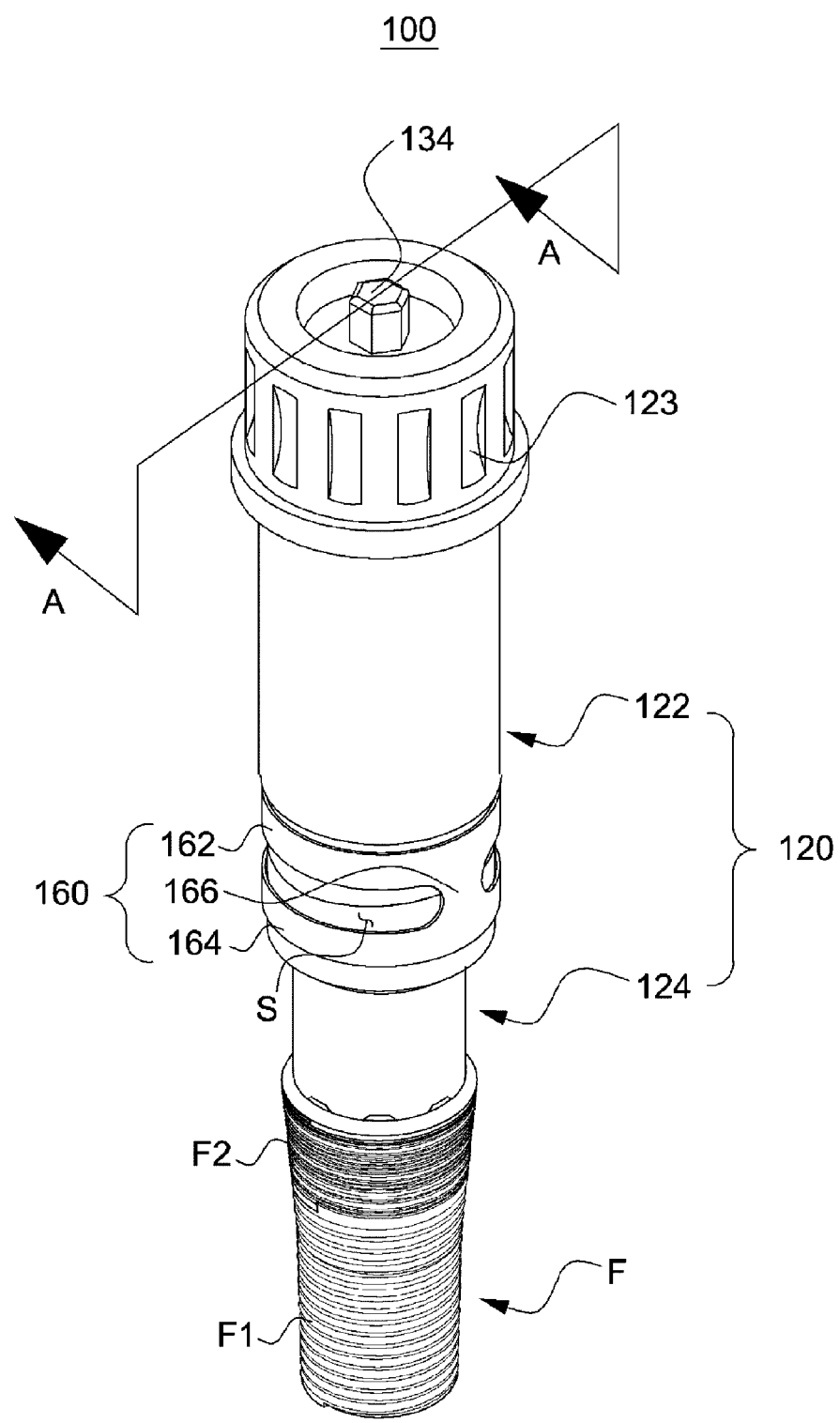
FIG. 1 is a schematic perspective view illustrating an implant fixture remover mounted on a fixture according to an exemplary embodiment of the present invention.

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention. Further, like reference numerals refer to like elements throughout the specification.

Figure 2:
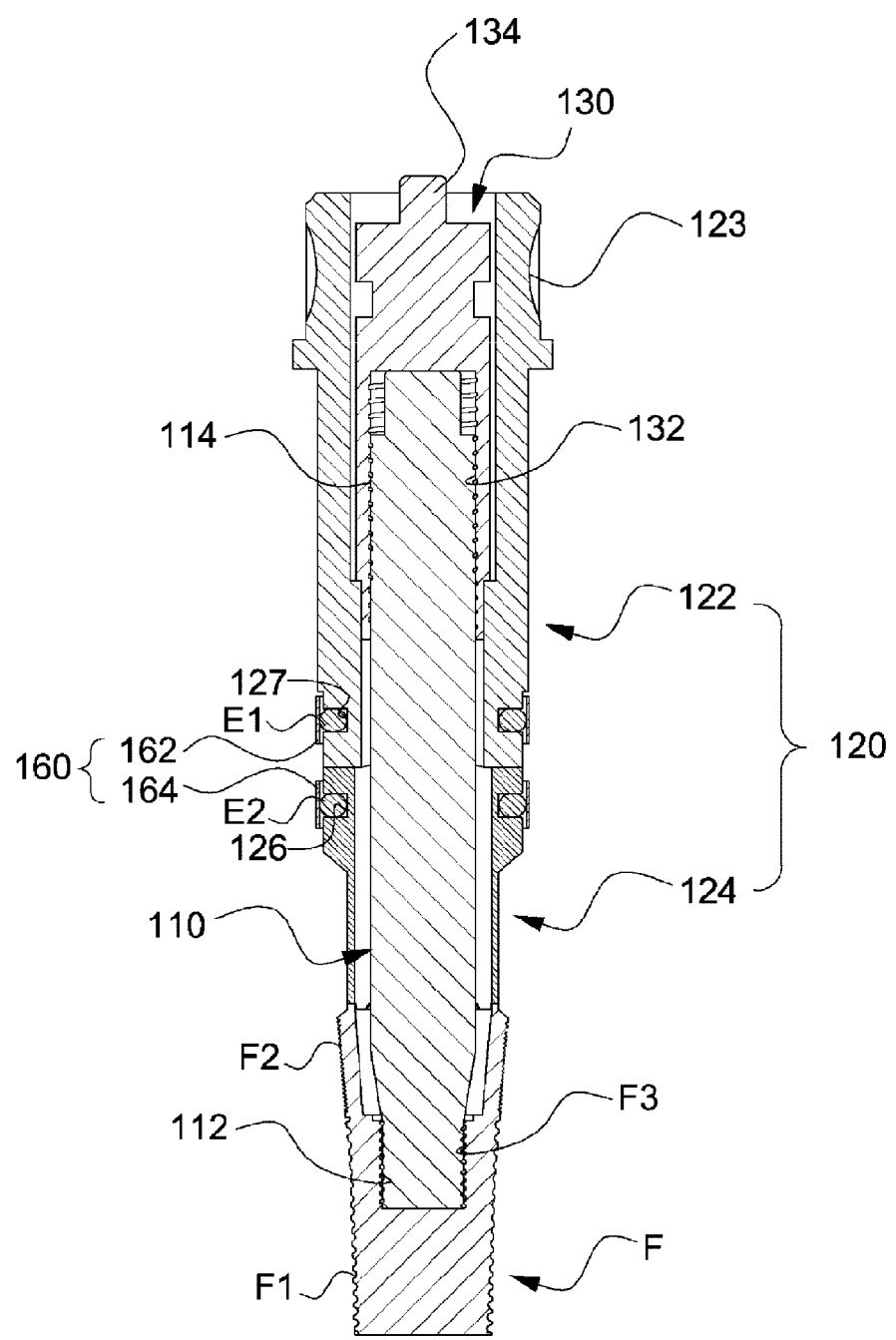
FIG. 2 is a schematic cross-sectional view taken along line AA of FIG. 1.
Figure 3:
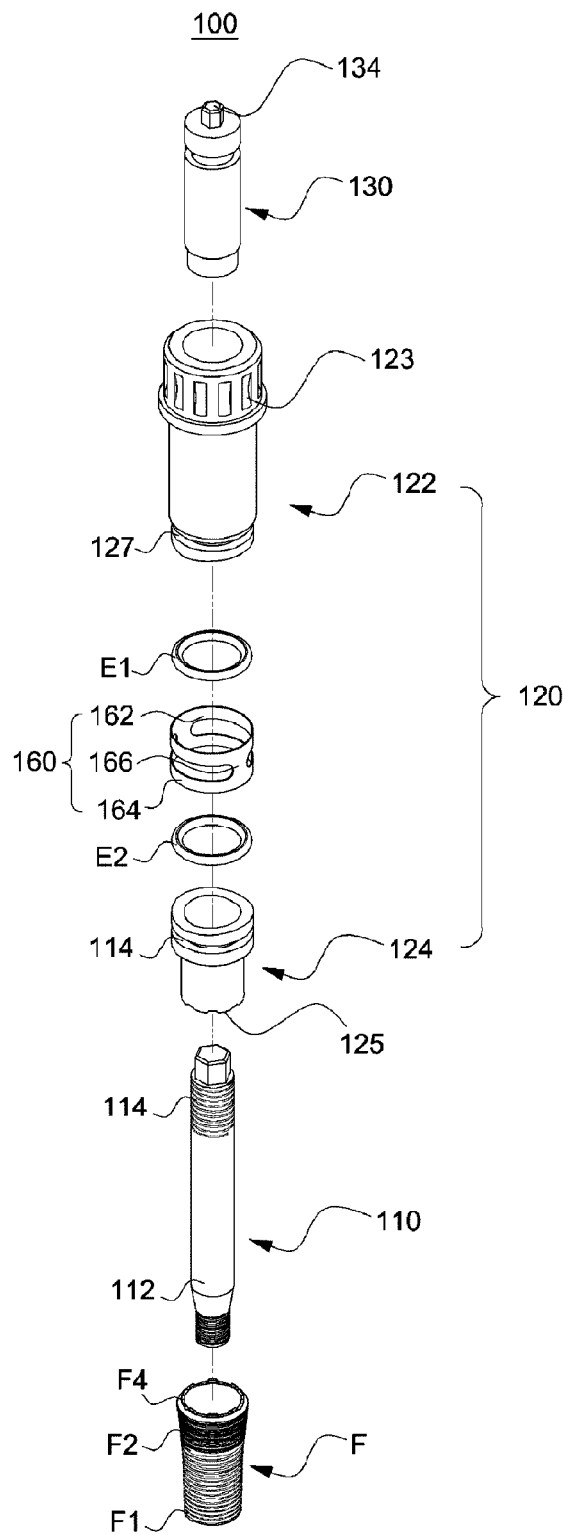
FIG. 3 is a schematic exploded perspective view (fixture included) illustrating the implant fixture remover according the an exemplary embodiment of the present invention.

FIG. 1 is a schematic perspective view illustrating an implant fixture remover according to an exemplary embodiment of the present invention mounted on a fixture, FIG. 2 is a schematic cross-sectional view taken along line AA of FIG. 1, and FIG. 3 is a schematic exploded perspective view (fixture included) illustrating the implant fixture remover according to the exemplary embodiment of the present invention.

Figure 4:
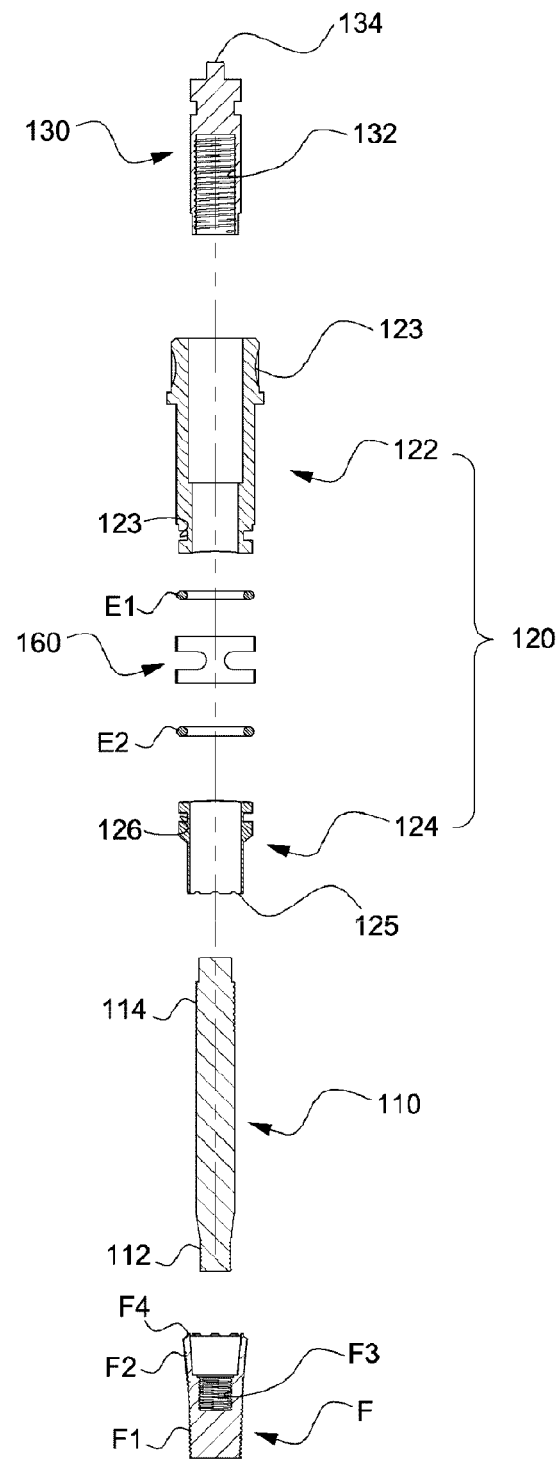
FIG. 4 is a schematic exploded perspective view illustrating the implant fixture remover according to the exemplary embodiment of the present invention.
Figure 5:
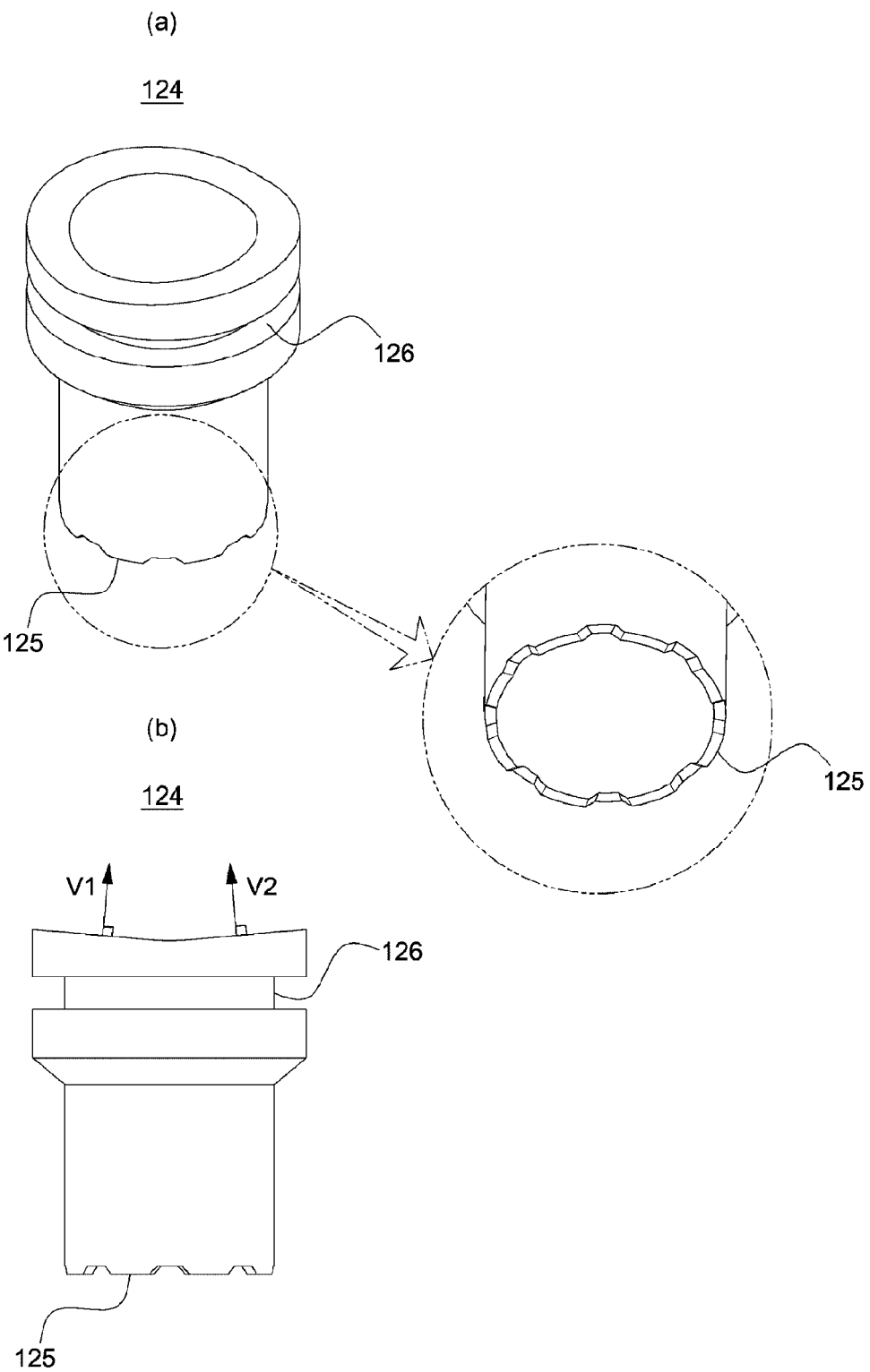
FIG. 5 is a schematic perspective view and a schematic side view illustrating a torque transmitting portion included in the implant fixture remover according to the exemplary embodiment of the present invention.
Figure 6:
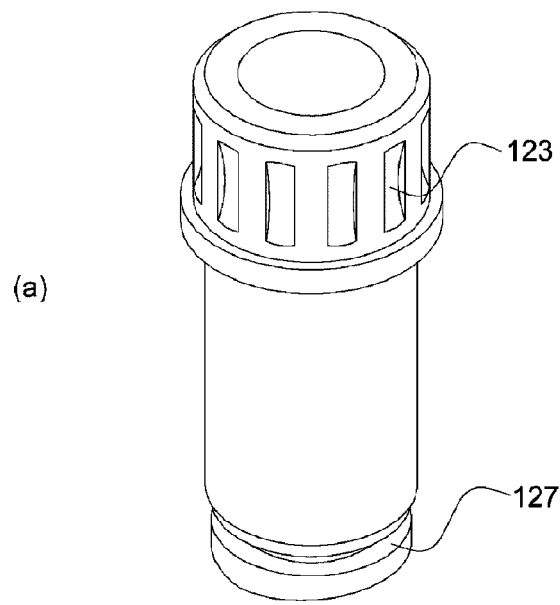
FIG. 6 is a schematic perspective view and a schematic side view illustrating a torque providing portion included in the implant fixture remover according to the exemplary embodiment of the present invention.
Figure 6:
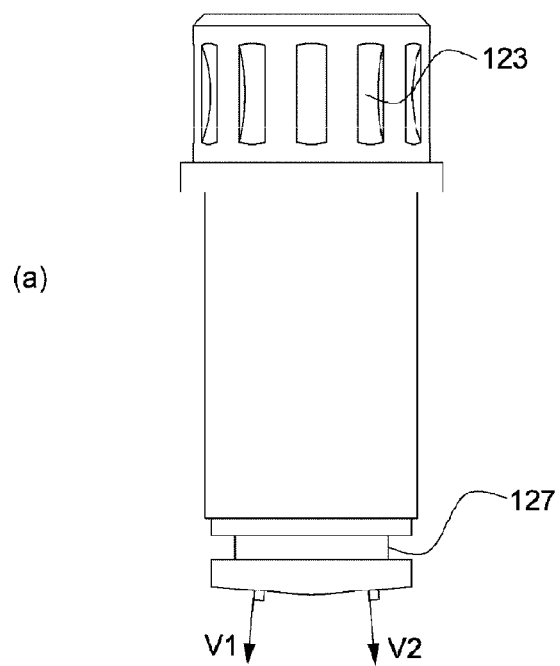

Further, FIG. 4 is a schematic exploded perspective view illustrating the implant fixture remover according to the exemplary embodiment of the present invention, FIG. 5 is a schematic perspective view and a schematic side view illustrating a torque transmitting portion included in the implant fixture remover according to the exemplary embodiment of the present invention and FIG. 6 is a schematic perspective view and a schematic side view illustrating a torque providing portion included in the implant fixture remover according to the exemplary embodiment of the present invention.

Referring to FIGS. 1 to 6, an implant fixture remover 100 according to the embodiment of the present invention may include a remover screw 110 having a first thread 112 and a second thread 114 respectively formed on one side and the other side of the remover screw, a remover driver 120 inserted into the remover screw 110 with variable location, and a driver fixing portion 130 coupled to the second thread 114.

First, an implant fixture F (hereinafter called "fixture") is inserted into an alveolar bone and fused thereto. In the fixture F, a right-handed thread may be formed on the outer circumferential surface of the fixture F so as to be screwed to a cortical bone and a trabecular bone.

However, a left-handed thread may be formed on the outer circumferential surface of the fixture F instead of the right-handed thread.

The right-handed thread formed on an outer circumferential surface of the fixture F may include a wide right-handed thread F1, and a narrow right-handed thread F2 formed to have a pitch distance smaller than the wide right-handed thread from the end of the wide right-handed thread. Accordingly, an implant time may be shortened upon implanting a fixture F, and thus, bone stress may be minimized. Further, an excellent initial fixing force may be provided.

Here, the implant time may be shortened by the narrow right-handed thread F2, and the initial fixing force may be ensured by the wide right-handed thread F1.

At least one cutting edge portion (not shown) formed in a length direction may be formed on the wide right-handed thread F1 of the fixture F, and when the fixture F is implanted into the alveolar bone using the cutting edge portion (not shown), an implantation may be further facilitated due to a sharp front end.

A groove having an open top surface with a predetermined depth may be formed in the fixture F, so that an artificial tooth crown is screwed to an upper side thereof. A thread may be formed on the inner circumferential surface of the groove, in other words, a female screw portion F3 may be formed.

A thread formed on the outer circumferential surface of the fixture F and the thread of the female screw portion F3 may be in the same direction, and for example, may be right-handed threads.

Hereinafter, each component of an implant fixture remover 100 according to the exemplary embodiment of the present will be described in detail.

The remover screw 110 may have a double screw shape with a predetermined length and may have a first thread 112 on one side thereof so as to be screwed to a female screw portion F3 implanted into an alveolar bone and a second thread 114 formed on the other side thereof.

Here, the first thread 112 and the second thread 114 may be formed in an opposite direction. When the first thread 112 is a right-handed thread, the second thread 114 may be a left-handed thread. When the first thread 112 is a left-handed thread, the second thread 114 may be a right-handed thread.

Here, directions of threads F1, F2 formed on an outer circumferential surface of a fixture F, a thread of a female screw portion F3 formed on an inner circumferential surface, the first thread 112 formed on one side of the remover screw 110, and the second thread 114 formed on the other side of the remover screw 110 may be composed by various combinations.

Hereinafter, a case in which the threads F1, F2 formed on the outer circumferential surface of the fixture F, the thread of the female screw portion F3 formed on the inner circumferential surface, and the first thread 112 formed on the one side of the remover screw 110 are the same right-handed threads, and the second thread 114 formed on the other side of the remover screw 110 is a left-handed thread will be described as an example.

A remover driver 120 may be inserted into the remover screw 110 screwed to the fixture F with variable location and may include a torque providing portion 122 generating a torque by an external force applied from outside and a torque transmitting portion 124 receiving the torque and maintaining contact with the fixture so that the fixture is extracted from the alveolar bone.

The torque transmitting portion 124 of the remover driver 120 is limited in variability of a position by a driver fixing portion 130 screwed to the second thread 114, and thus, the torque transmitting portion 124 may maintain contact with the fixture F.

In other words, the remover driver 120 is slide-inserted into the remover screw 110 and becomes in contact with the fixture F by self-weight before the driver fixing portion 130 is screwed to the second thread 114, the remover driver 120 is pressurized toward the fixture F as the driver fixing portion 130 is turned to be screwed to the second thread 114, and thus, the remover driver 120 may be maintained so that the remover driver 120 is in contact with the fixture F.

Here, the reason why the remover driver 120 is pressurized toward the fixture F as the driver fixing portion 130 is turned to be screwed to the second thread 114 is that the driver fixing portion 130 becomes in contact with an inner side of the remover driver 120. In other word, when the driver fixing portion 130 moves toward the fixture F as the driver fixing portion 130 is screwed to the second thread 114, a pressure toward the fixture F is applied to the remover driver 120 accordingly.

More specifically, when the driver fixing portion 130 moves toward the fixture F as the driver fixing portion 130 is turned to be screwed to the second thread 114, the torque providing portion 122 in contact with the driver fixing portion 130 pressurizes the torque transmitting portion 124, and as a result, the torque transmitting portion 124 pressurizes the fixture F while contacting the fixture F.

On the other hand, the torque providing portion 122 and the torque transmitting portion 124 may be connected to each other by a connection portion 160 so that the torque providing portion 122 and the torque transmitting portion 124 coact before being slide-inserted into the remover screw 110.

The connection portion 160 may allow facing surfaces of the torque transmitting portion 124 and the torque providing portion 122 to be in contact with each other.

Here, the torque providing portion 122 and the torque transmitting portion 124 respectively include a first concavity 127 and a second concavity 126 recessed in a circumferential direction, and a first elastic ring E1 and a second elastic ring E2, which are elastically deformed by contacting the connection portion 160, may be inserted into the first concavity 127 and the second concavity 126, respectively, so that the torque providing portion 122 and the torque transmitting portion 124 are temporarily fixed to coact by the connection portion 160.

The first elastic ring E1 and the second elastic ring E2 may be a kind of O-ring (i.e., rubber ring), and the connection portion 160 may include a first close-coupling portion 162 and a second close-coupling portion 164 contacting the first elastic ring E1 and the second elastic ring E2, respectively, and a close-coupling connection 166 connecting the first close-coupling portion 162 to the second close-coupling portion 164.

One or more of the close-coupling connections 166 may be formed to have a space portion S formed between the first close-coupling portion 162 and the second close-coupling portion 164 so that the facing surfaces of the first close-coupling portion 162 and the second close-coupling portion 164 may be determined with the naked eye. When the close-coupling connection 166 is provided in a plural number, the close-coupling connections 166 may be formed spaced apart from each other.

Accordingly, since the facing surfaces may be seen through the space portion S when the torque providing portion 122 and the torque transmitting portion 124 are connected to fix temporarily in the connection portion 160, convenience may be maximized for temporary fixing.

On the other hand, the torque transmitting portion 124 of the remover driver 120 may include a concave-convex contact surface 125 so that a contact force with the fixture F is increased, and the fixture F may have a shape F4 corresponding to the concave-convex contact surface 125 so that the concave-convex contact surface 125 is inserted into the fixture F.

As a result, when the remover driver 120 is turned so that the fixture F is turned to be extracted from the alveolar bone, a friction force effectively works in a direction in which the concave-convex contact surface 125 is closely coupled to and burrowing into an upper side of the fixture F, and thus, a fixture F may be rapidly and simply extracted from the alveolar bone while minimizing loss of the alveolar bone.

The concave-convex contact surface 125 formed on the torque transmitting portion 124 may be formed in a variety of shapes such as a square-wave shape or a saw-toothed shape.

Figure 14:
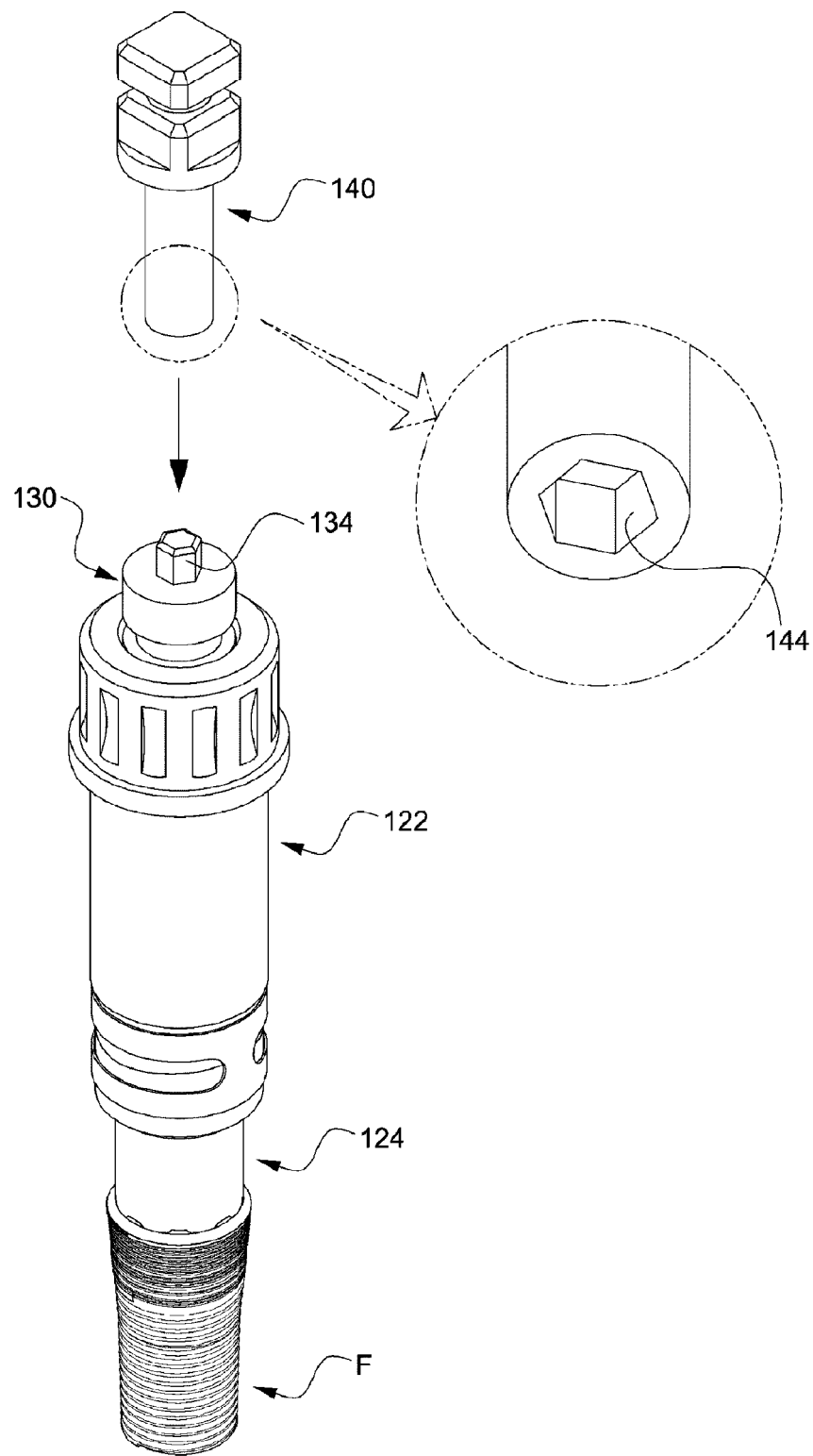
Figure 15:
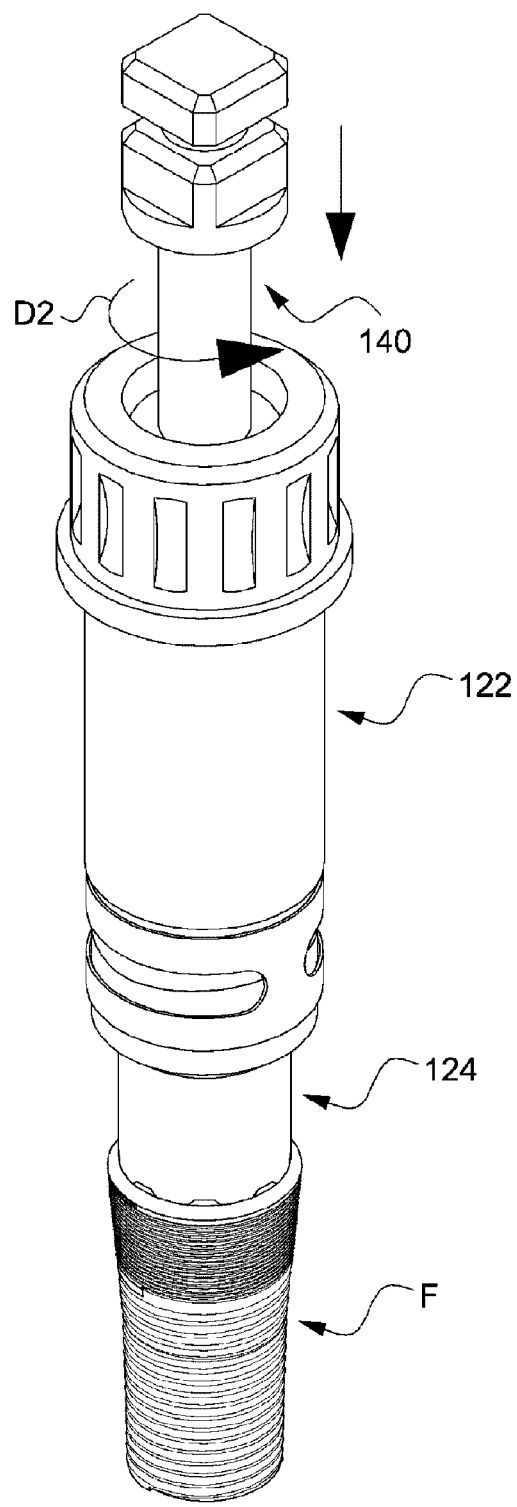

On the other hand, the driver fixing portion 130 may be screwed to the second thread 114 through a coupling portion 140 (refer to FIGS. 14 and 15) detachably mounted on the driver fixing portion 130.

Here, a female screw portion 132 for screw coupling with the second thread 114 may be formed on one side of the driver fixing portion 130, and a detachable portion 134 having a polygonal shape to engage with the coupling portion 140 may be formed on the other side of the driver fixing portion 130.

The coupling portion 140 may include a corresponding detachable portion 144 (refer to FIG. 14) formed corresponding to the detachable portion 134. After the driver fixing portion 130 is inserted into the torque providing portion 122 and the detachable portion 134 is inserted into the corresponding detachable portion 144 to engage therewith, the driver fixing portion 130 may be screwed to the second thread 114 by turning the coupling portion 140 in a direction of a left-handed thread.

As a result, the concave-convex contact surface 125 of the torque transmitting portion 124 may become in contact with an upper side of the fixture F by turning the coupling portion 140.

On the other hand, when the driver fixing portion is screwed to the second thread 114 by turning the coupling portion 140, and thus, the torque transmitting portion 124 maintains contact with the fixture F, the torque providing portion 122 may be turned using a wrench portion 150 (refer to FIGS. 16 and 17) after separating the coupling portion 140 from the driver fixing portion 130.

The wrench portion 150 may be a component which may extract the fixture F from the alveolar bone by being turned while detachably mounted on the torque providing portion 122 of the remover driver 120, through the torque transmitting portion 124 of the remover driver 120 maintaining contact with the fixture F as a medium. Thus, the torque providing portion 122 may include a binding portion 123 which binds the wrench portion 150.

The binding portion 123 may have a groove shape, and the wrench portion 150 and the torque providing portion 122 may be turned by coacting through a construction in which protrusions 152 (refer to FIG. 16) of the wrench portion 150 are inserted into the grooves.

However, a shape of the binding portion 123 is not limited to a groove and may be modified variously, such as to a protrusion, etc.

The torque providing portion 122 may also be turned in a left-handed thread direction by turning the wrench portion 150 in the left-handed thread direction. The torque transmitting portion 124 receives a force toward the fixture F at the same time as when the torque transmitting portion 124 is turned by turning the torque providing portion 122, and thus, the torque transmitting portion 124 may extract the fixture from the alveolar bone by turning the fixture F in the left-handed thread direction, while contacting the fixture F.

Due to a construction of facing surfaces of the torque providing portion 122 and the torque transmitting portion 124, the force toward the fixture F may be generated at the same time as when the torque transmitting portion 124 is turned by turning the torque providing portion 122. The facing surfaces of the torque providing portion 122 and the torque transmitting portion 124 may be formed curved based on the central axis.

Further, the facing surfaces of the torque providing portion 122 and the torque transmitting portion 124 may be defined by at least two normal vectors V1, V2, and an outer end with respect to the facing surfaces of the torque providing portion 122 and the torque transmitting portion 124 may form a triangular wave or a sine wave.

Due to the above-described construction of the facing surfaces of the torque providing portion 122 and the torque transmitting portion 124, a torque of the torque providing portion 122 generated by turning the wrench portion 150 may work as a repulsive force to the facing surfaces and thus, may provide the torque transmitting portion 124 with an applied pressure toward the fixture F. Accordingly, the fixture F may be extracted from the alveolar bone by turning the fixture F in the left-handed thread direction while contacting the torque transmitting portion 124.

Hereinafter, an extraction process of a fixture F by an implant fixture remover 100 according to an exemplary embodiment of the present invention will be described in steps.

FIGS. 7 to 17 are schematic views for describing a method of using the implant fixture remover according to the exemplary embodiment of the present invention.

Figure 7:
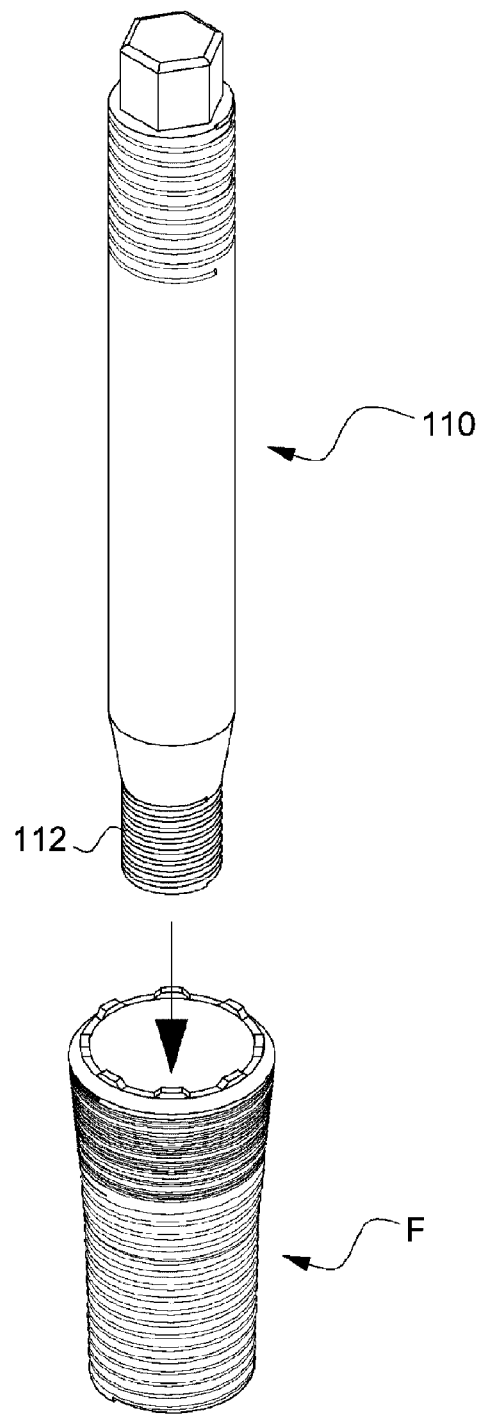
FIGS. 7 to 17 are schematic views for describing a method of using an implant fixture remover according to an exemplary embodiment of the present invention.
Figure 8:
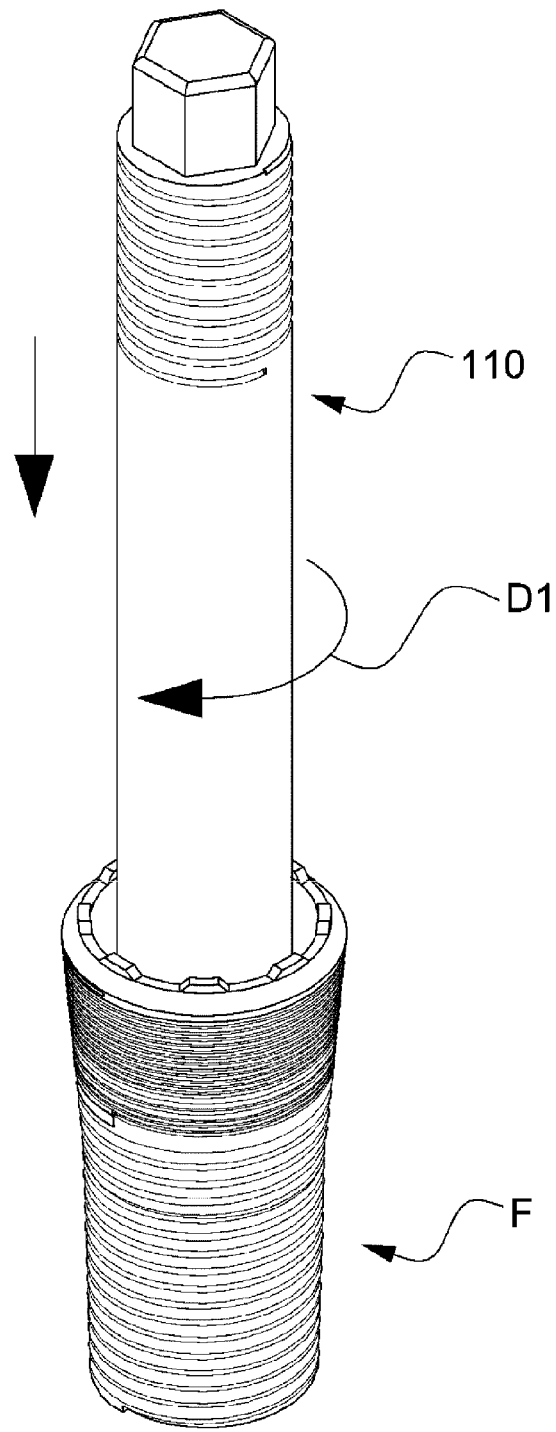

Referring to FIGS. 7 and 8, first, a first thread 112 of a remover screw 110 is screwed to a female screw portion F3 of a fixture F implanted into an alveolar bone.

Here, since the female screw portion F3 and the first thread 112 may be in a direction of a right-handed thread D1, the first thread 112 may be screwed to the female screw portion F3 by turning the remover screw 110 in the direction of the right-handed thread D1.

Figure 9:
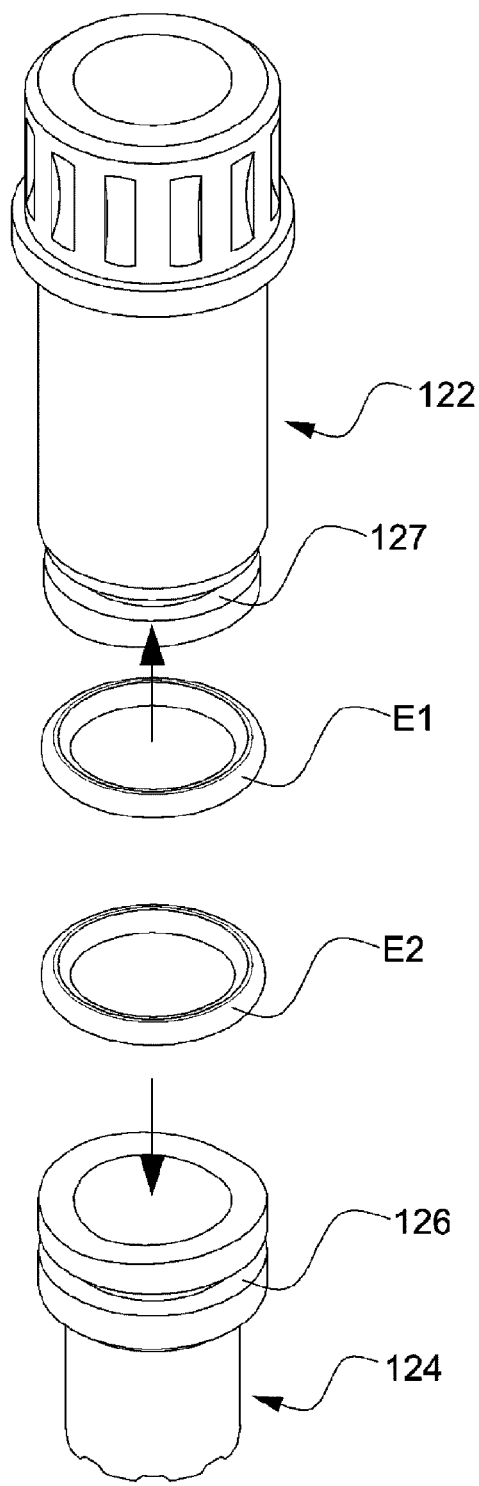
Figure 10:
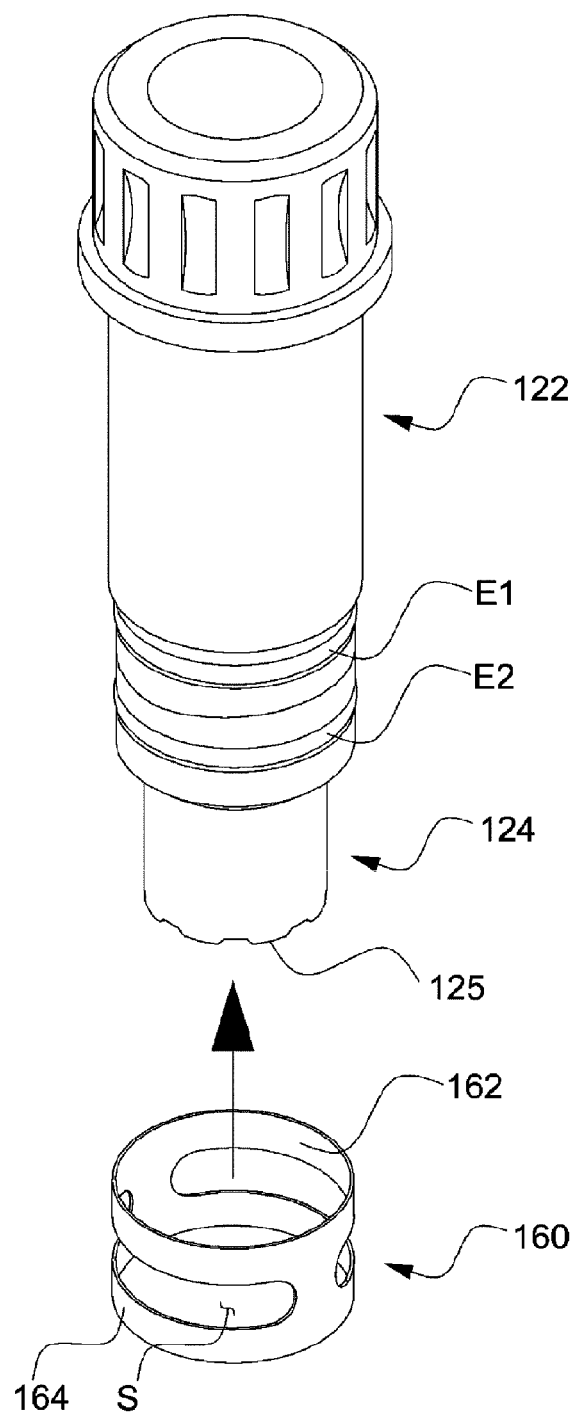
Figure 11:
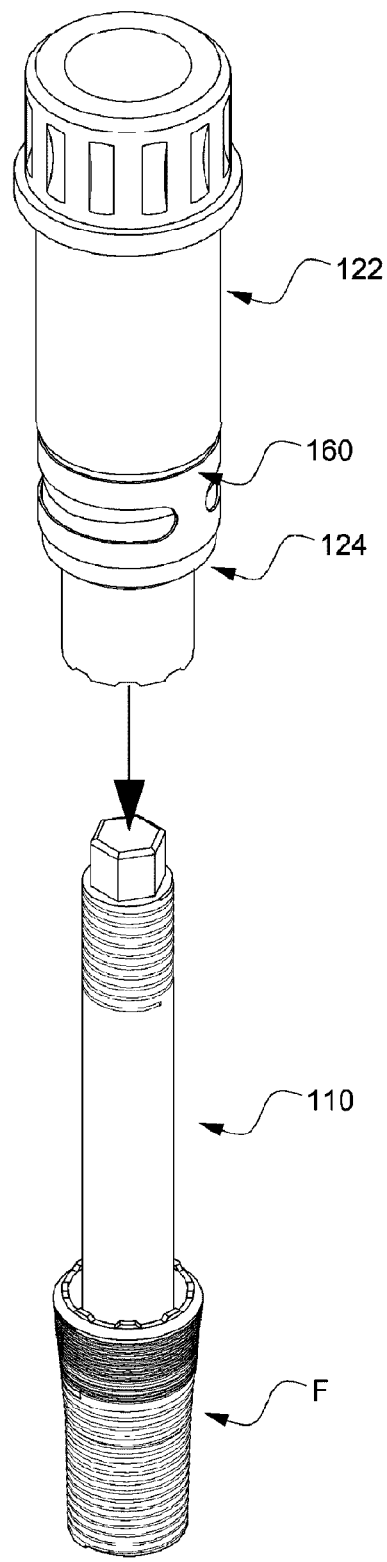
Figure 12:
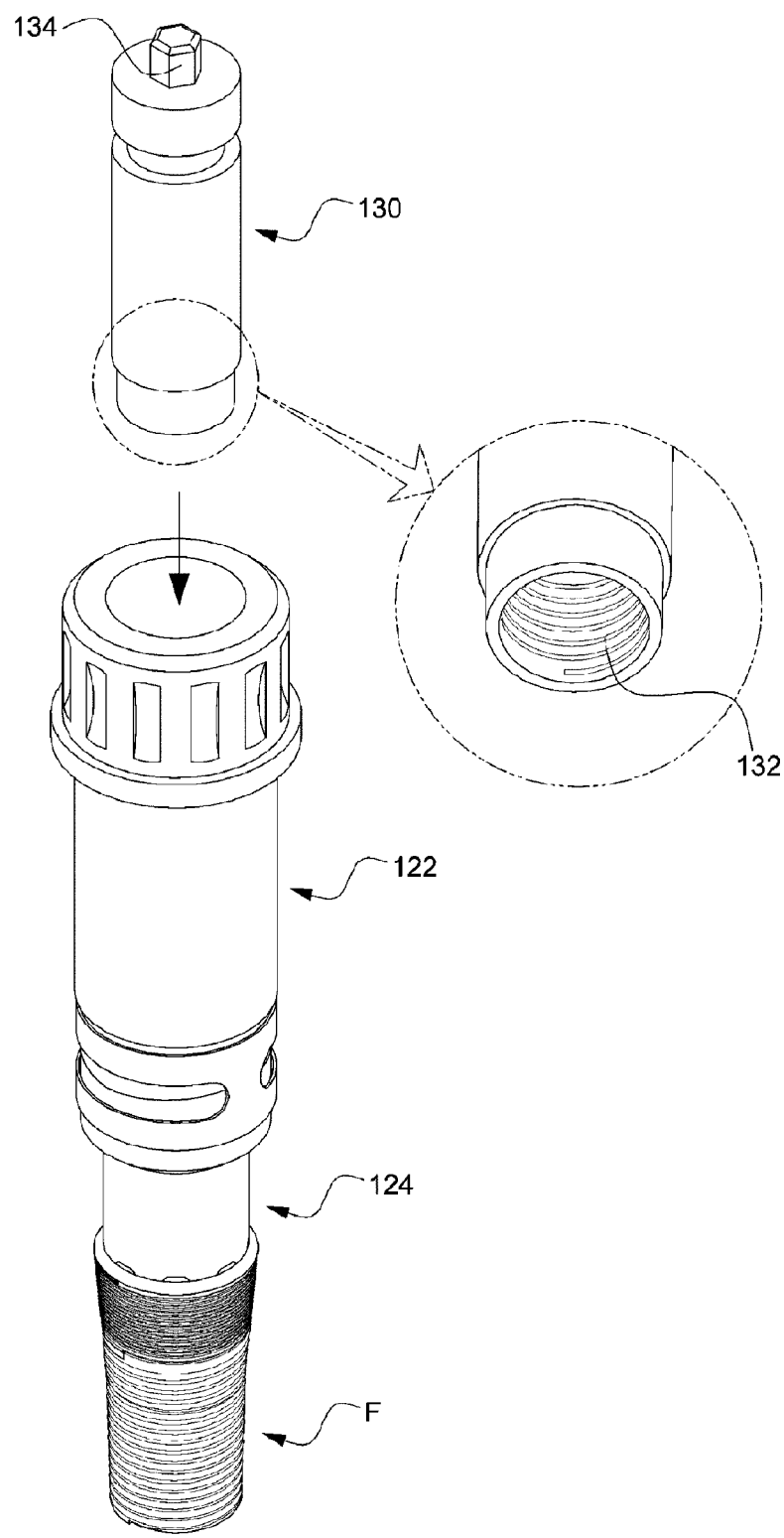
Figure 13:
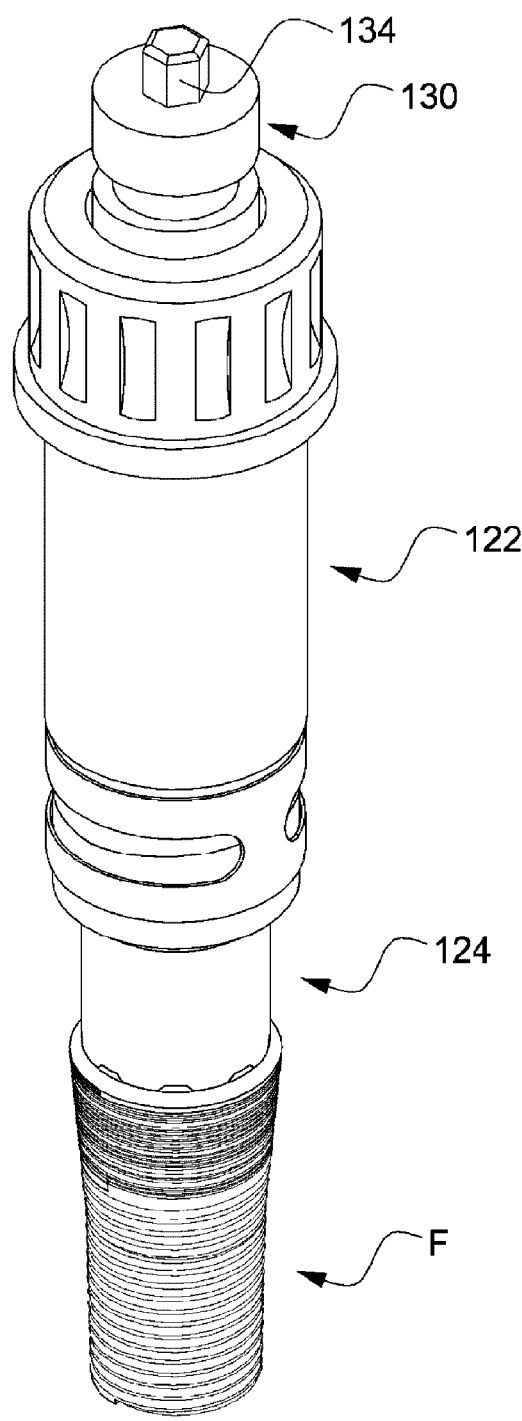

Referring to FIGS. 9 to 11, a torque transmitting portion 124 and a torque providing portion 122 are temporarily fixed so that a remover driver 120 is slide-inserted into the remover screw 110.

A first elastic ring E1 is inserted into a first concavity 127 of the torque providing portion 122 of the remover driver 120, and a second elastic ring E2 is inserted into a second concavity 126 of the torque transmitting portion 124 of the remover driver 120.

After the first elastic ring E1 and the second elastic ring E2 are inserted into the first concavity 127 and the second concavity 126, respectively, the torque providing portion 122 and the torque transmitting portion 124 are temporarily fixed by a connection portion 160.

Here, a first close-coupling portion 162 of the connection portion 160 may become in contact with the first elastic ring E1, a second close-coupling portion 164 of the connection portion 160 may become in contact with the second elastic ring E2, and it may be determined through a space portion S whether facing surfaces are well aligned.

After the torque transmitting portion 124 and the torque providing portion 122 temporarily fixed by the connection portion 160 as described above are inserted into the remover screw 110, an concave-convex contact surface 125 of the torque transmitting portion 124 may become in contact with an upper end of the fixture F by self-weight.

Referring to FIGS. 12 to 15, after the torque transmitting portion 124 and the torque providing portion 122 are inserted into the remover screw 110, a remover fixing portion 130 is inserted into the torque providing portion 122.

After the remover fixing portion 130 is inserted into the torque providing portion 122, a detachable portion 134 of the remover fixing portion 130 is inserted into a corresponding detachable portion 144 of a coupling portion 140 to engage therewith, and subsequently, the coupling portion 140 is turned in a direction of a left-handed thread D2.

A female screw portion 132 of the remover fixing portion 130 may be screwed to a second thread 114 of the remover screw 110 by turning the coupling portion 140, and accordingly, a location movement of the torque transmitting portion 124 is limited on a remover screw 110. Thus, the torque transmitting portion 124 may maintain contact with the fixture F.

When the torque transmitting portion 124 pressurizes the fixture F, and maintains contact with the fixture F, the coupling portion 140 is separated from the driver fixing portion 130.

Figure 16:
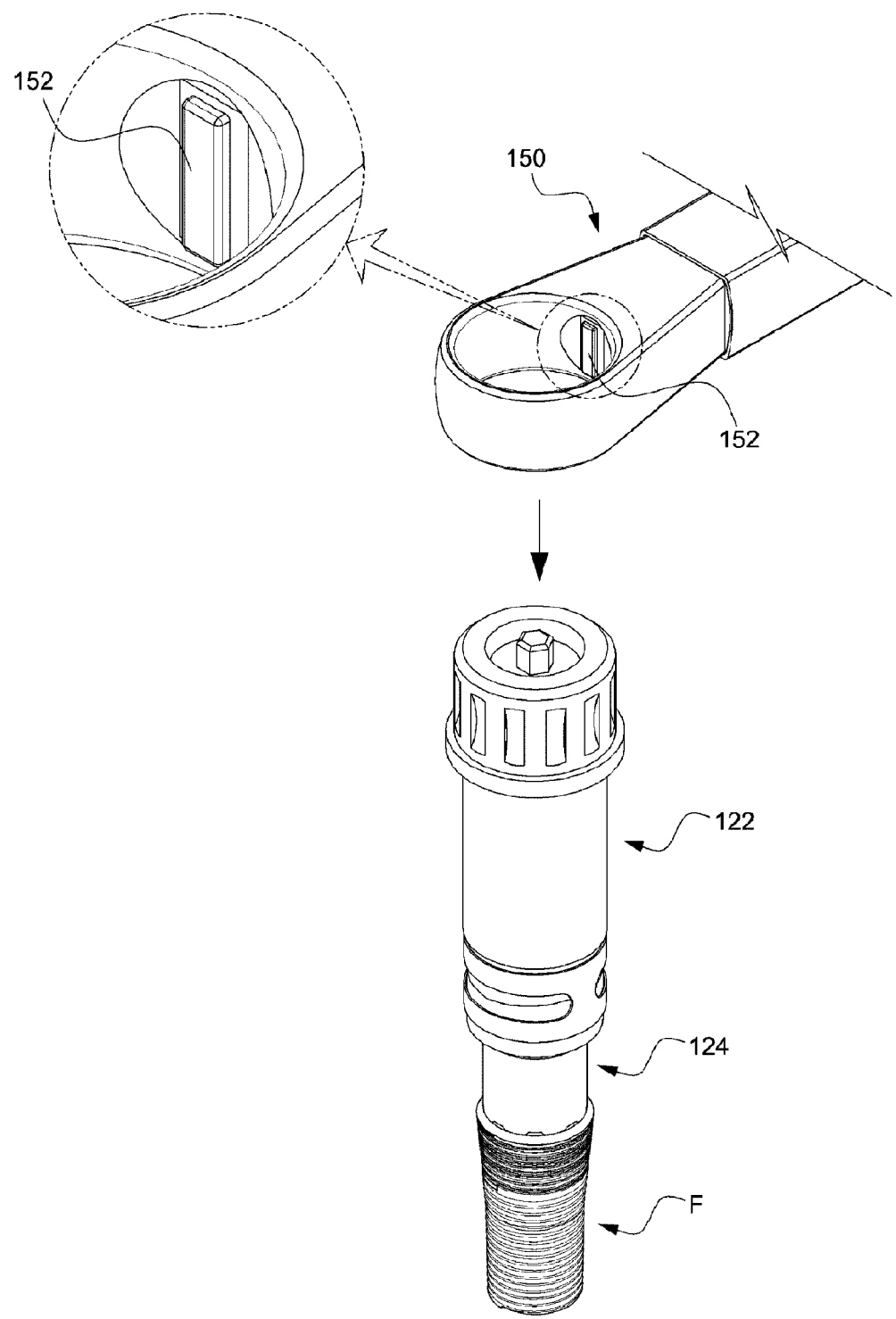
Figure 17:
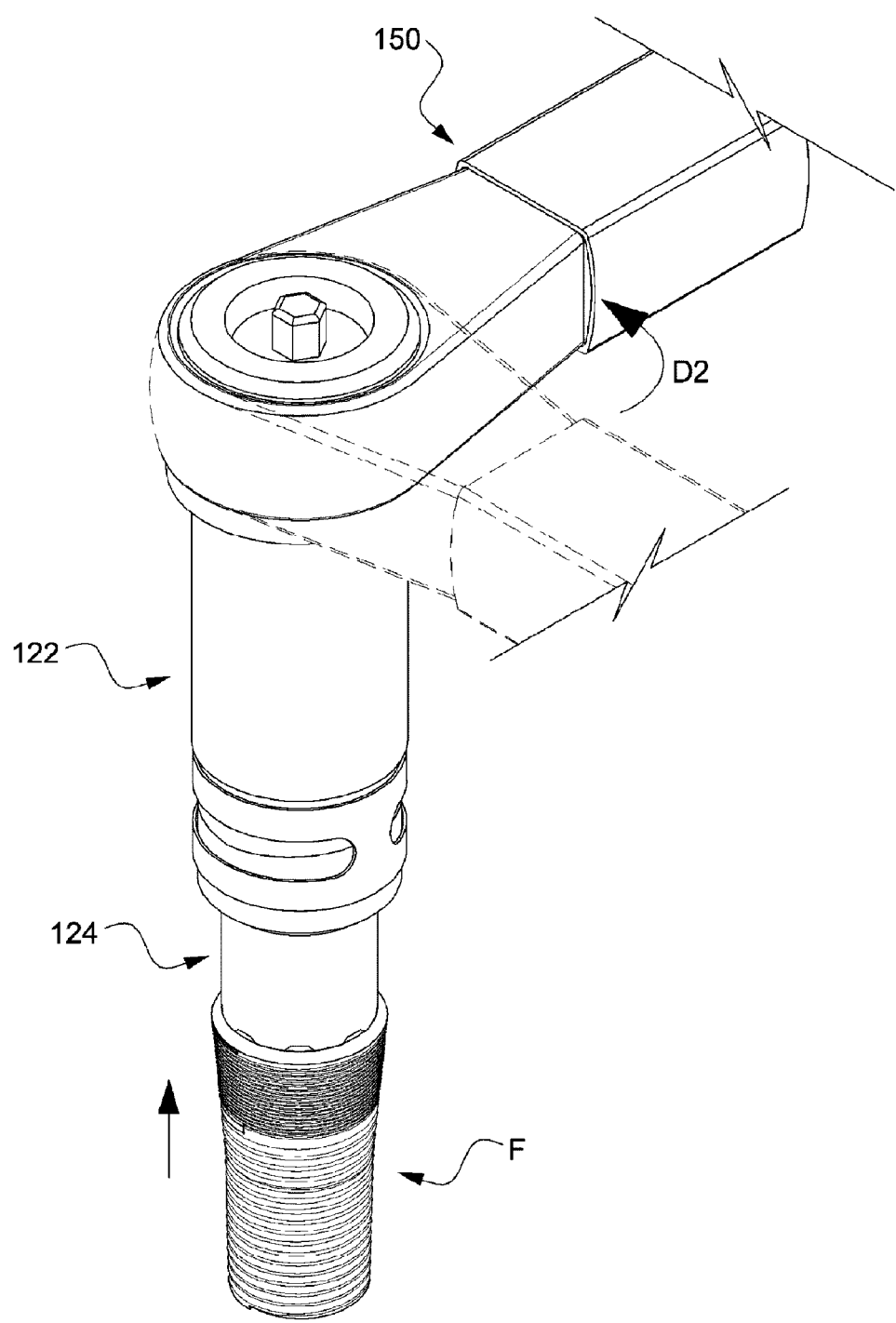

Referring to FIGS. 16 and 17, after the torque transmitting portion 124 becomes in contact with the fixture F, the torque providing portion 122 may be turned in the direction of the left-handed thread D2 using a wrench portion 150.

Here, the torque transmitting portion 124 receives a pressure applied toward the fixture F at the same time as when the torque transmitting portion 124 is turned by turning the torque providing portion 122 and pressurizes the fixture F while contacting the fixture F and turns the fixture F in the direction of the left-handed thread D2, and thus, the fixture F may be extracted from the alveolar bone.

Here, since a force generated toward the fixture F at the same time as when the torque transmitting portion 124 is turned by turning the torque providing portion 122 was described above, detailed descriptions thereof will not be repeated.

Figure 18:
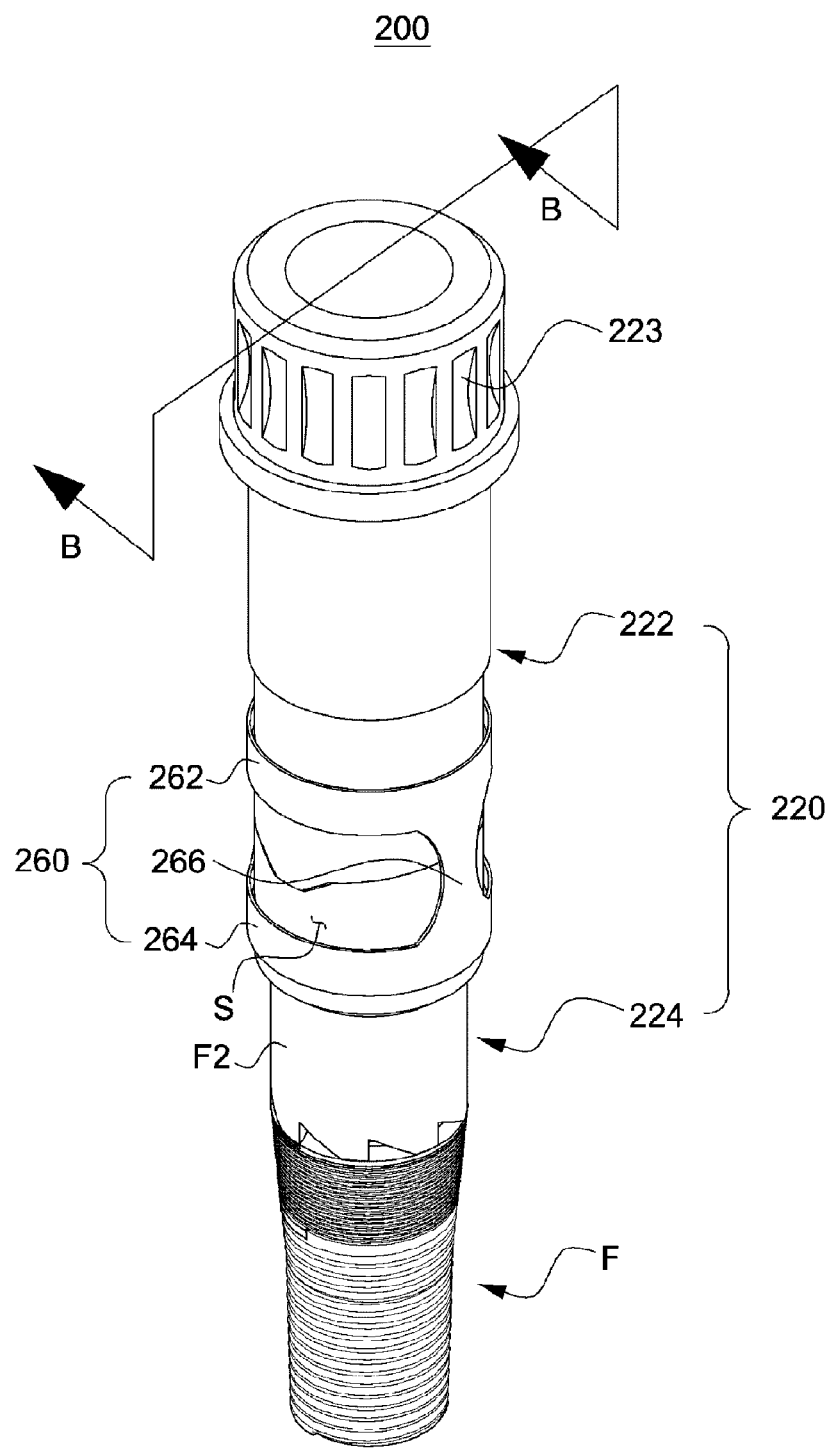
FIG. 18 is a schematic perspective view illustrating an implant fixture remover according to another exemplary embodiment of the present invention mounted on a fixture.
Figure 19:
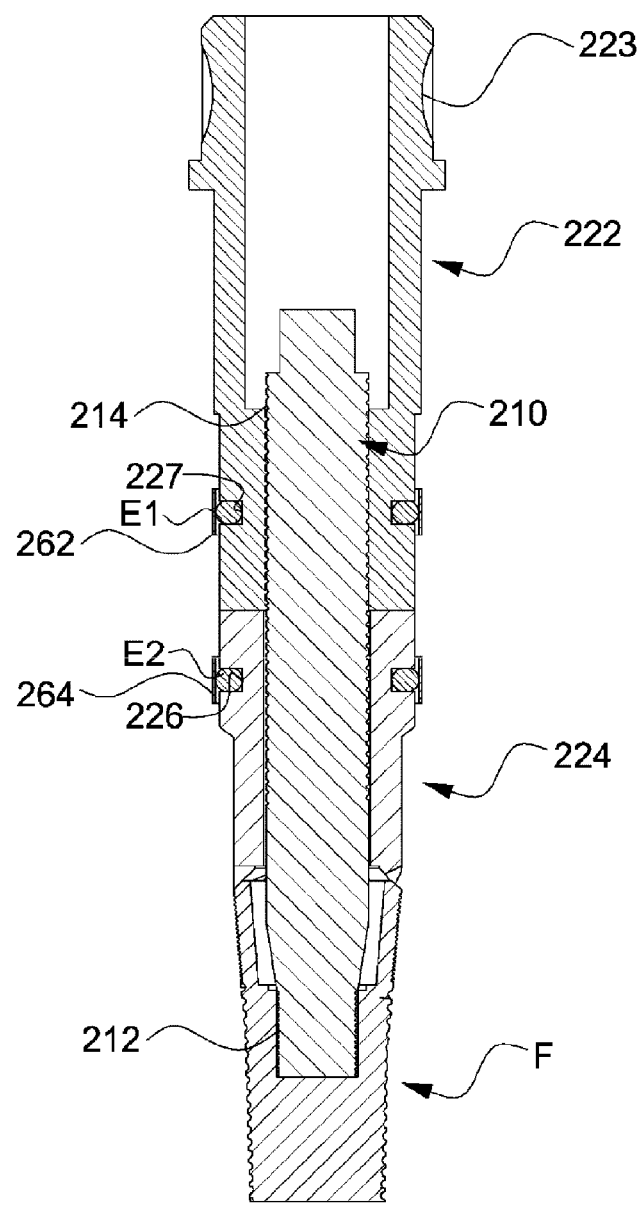
FIG. 19 is a schematic cross-sectional view taken along line BB of FIG. 18.
Figure 20:
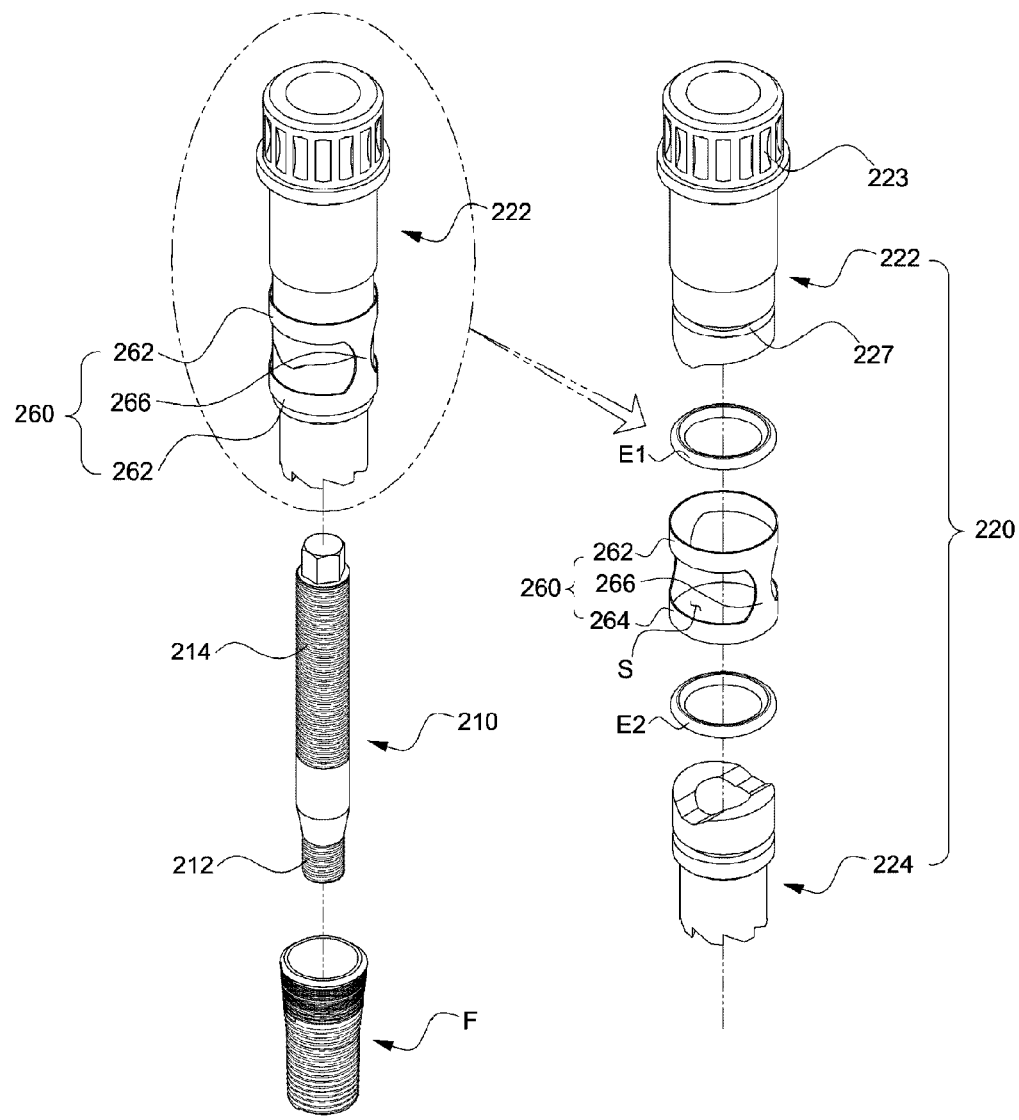
FIG. 20 is a schematic exploded perspective view (fixture included) illustrating an implant fixture remover according to another exemplary embodiment of the present invention.

FIG. 18 is a schematic perspective view illustrating an implant fixture remover according to another exemplary embodiment of the present invention mounted on a fixture, FIG. 19 is a schematic cross-sectional view taken along line BB of FIG. 18, and FIG. 20 is a schematic exploded perspective view (fixture included) illustrating an implant fixture remover according to another exemplary embodiment of the present invention.

Figure 21:
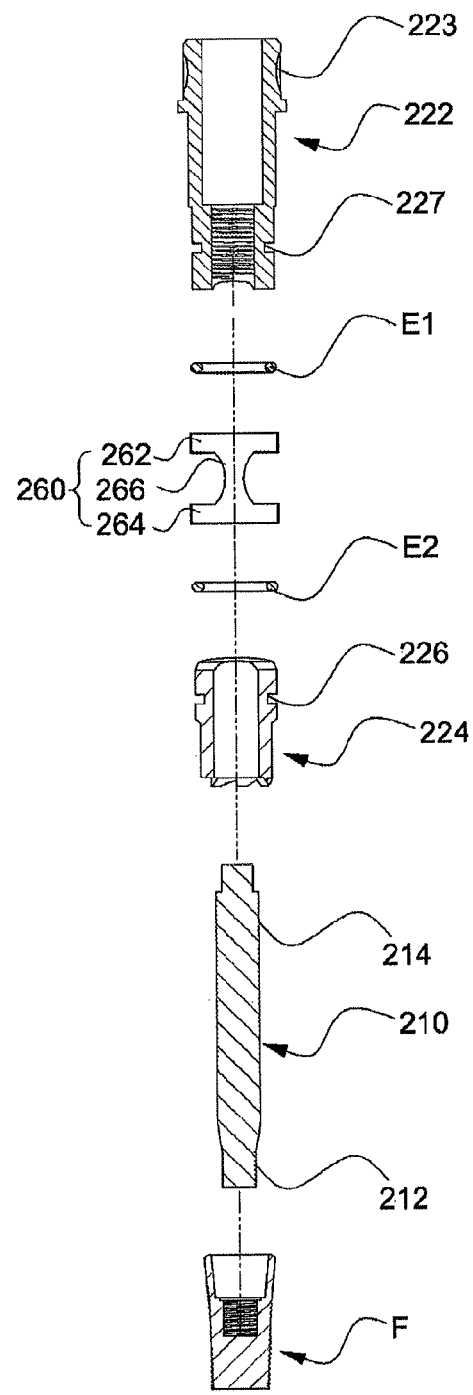
FIG. 21 is a schematic exploded perspective view illustrating an implant fixture remover according to another exemplary embodiment of the present invention.
Figure 22:
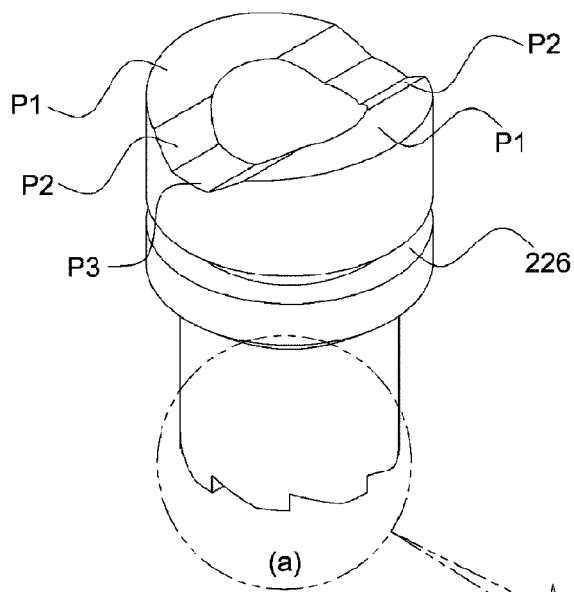
FIG. 22 is a schematic perspective view and a schematic side view illustrating a torque transmitting portion provided for an implant fixture remover according to another exemplary embodiment of the present invention.
Figure 22:
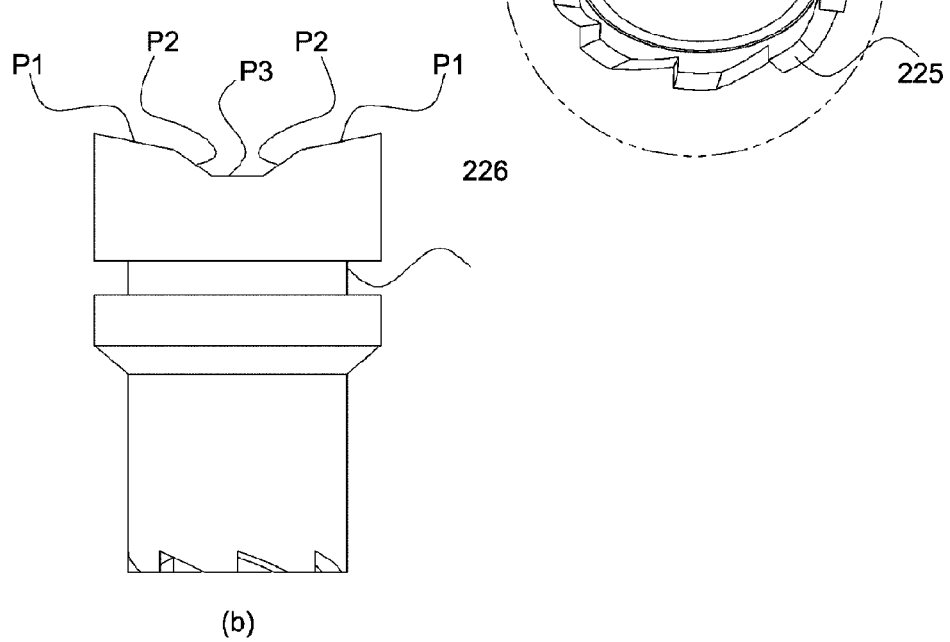
Figure 23:
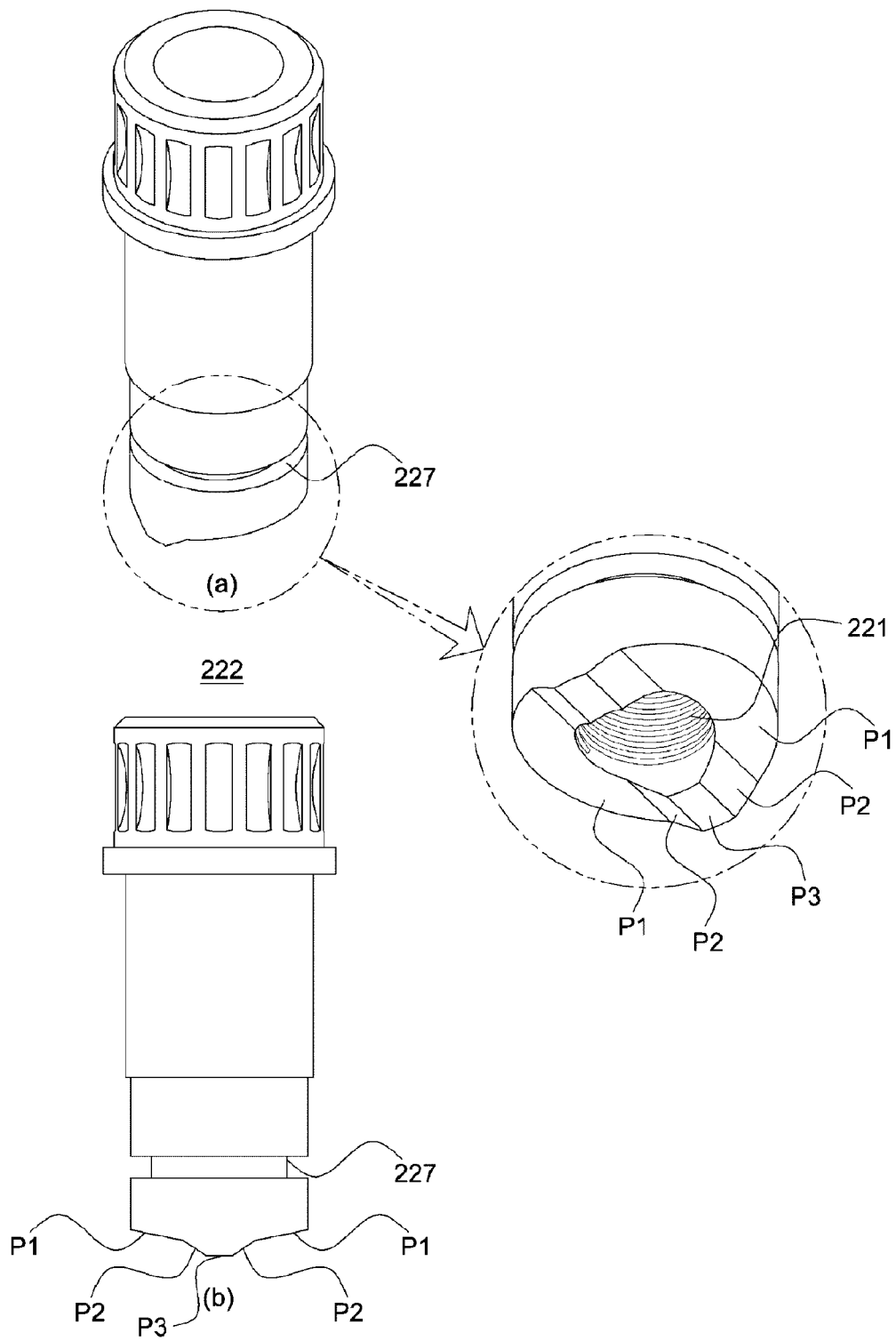
FIG. 23 shows a schematic perspective view and a schematic side view illustrating a torque providing portion provided for an implant fixture remover according to another exemplary embodiment of the present invention.

Further, FIG. 21 is a schematic exploded perspective view illustrating an implant fixture remover according to another exemplary embodiment of the present invention, FIG. 22 is a schematic perspective view and a schematic side view illustrating a torque transmitting portion provided for an implant fixture remover according to another exemplary embodiment of the present invention, and FIG. 23 shows a schematic perspective view and a schematic side view illustrating a torque providing portion provided for an implant fixture remover according to another exemplary embodiment of the present invention.

Referring to FIGS. 18 to 23, an implant fixture remover 200 according to another exemplary embodiment of the present invention may include a first thread 212 and a second thread 214 respectively formed on one side and the other side of the remover screw 210, and a remover driver 220 having a torque transmitting portion 224 slide-inserted into the remover screw 210 and a torque providing portion 222 formed separated from the torque transmitting portion 224.

Here, since the remover screw 210 has the same construction and effect as the remover screw 110 described in reference to FIGS. 1 to 17 except a total length of a first thread 212 and a second thread 214, detailed descriptions thereof will not be repeated.

The remover driver 220 may include a torque transmitting portion 224 slide-inserted into the remover screw 210, and a torque providing portion 222 formed separated from the torque transmitting portion 224 and screwed to the second thread 214 of the remover screw 210 so that the torque transmitting portion 224 maintains contact with the fixture F.

Here, after the torque providing portion 222 is screwed to the second thread 214, a force, which is applied to facing surfaces of the torque providing portion 222 and the torque transmitting portion 224 by a torque generated by turning the torque providing portion 222, is transmitted to the fixture F through the torque transmitting portion 224 and works as a repulsive force so that the fixture F is extracted from the alveolar bone, and thus, the torque transmitting portion 224 may be pressurized toward the fixture F.

Specifically, a degree of a slide-insertion of the torque transmitting portion 224 into the remover screw 210 may be determined by a degree of a coupling of a female screw portion 221 of the torque providing portion 222 to the second thread 214. Thus, the torque transmitting portion 224 and the torque providing portion 222 may be temporarily fixed by a connection portion 260.

The connection portion 260 may connect the torque transmitting portion 224 and the torque providing portion 222 so that the torque providing portion 222 is screwed to the second thread 214 while the torque transmitting portion 224 and the torque providing portion 222 coact, and the connection portion 260 may allow the facing surfaces to be in contact with each other before the torque providing portion 222 is screwed to the second thread 214.

Here, the torque providing portion 222 and the torque transmitting portion 224 may respectively include a first concavity 227 and a second concavity 226 recessed in a circumferential direction, and a first elastic ring E1 and a second elastic ring E2, which are elastically deformed by contacting the connection portion 260, may be inserted into the first concavity 227 and the second concavity 226, respectively, so that the torque providing portion 222 and the torque transmitting portion 224 are temporarily fixed to coact by the connection portion 260.

The first elastic ring E1 and the second elastic ring E2 may be a kind of O-ring (i.e., rubber ring), the connection portion 260 may include a first close-coupling portion 262 and a second close-coupling portion 264 in contact with the first elastic ring E1 and a second elastic ring E2, respectively, and a close-coupling connection 266 connecting the first close-coupling portion 262 and the second close coupling portion 264.

One or more of the close-coupling connection 266 may be formed to have a space portion S formed eye between the first close-coupling portion 262 and the second close-coupling portion 264 so that the facing surfaces of the first close-coupling portion 262 and the second close-coupling portion 264 may be determined with the naked eye. When the close-coupling connection 266 is provided in a plural number, the close-coupling connections 266 may be formed spaced apart from each other.

Accordingly, since the facing surfaces may be seen through the space portion S when the torque providing portion 222 and the torque transmitting portion 224 are connected to fix temporarily by the connection portion 260, convenience may be maximized for temporary fixing.

On the other hand, the facing surfaces of the torque providing portion 222 and the torque transmitting portion 224 may be defined by at least two normal vectors V1, V2 and formed corresponding to each other and formed symmetrically based on a virtual plane including a central axis.

Specifically, the facing surfaces may include a first facing surface P1 having a first slope based on the central axis, a second facing surface P2 which is formed continuously with the first facing surface P1 and has a second slope greater than the first slope, and a third facing surface P3 which is formed continuously with the second facing surface P2 and has a third slope greater than the second slope. The third facing surface P3 may be perpendicular to the virtual plane including the central axis.

A plurality of each of the first facing surface P1, the second facing surface P2, and the third facing surface P3 may be formed spaced apart from each other. The number of the third facing surfaces P3 may be smaller than that of the first facing surface P1 and the second facing surface P2.

On the other hand, when a fixture F is extracted from an alveolar bone by turning a wrench portion 250 (refer to FIG. 30 and FIG. 31) bound to a binding portion 223 formed on one side of the torque providing portion 222, the torque transmitting portion 224 may include a concave-convex contact surface 225 so that a contact force with the fixture F is increased.

As a result, when the torque providing portion 222 is turned by the wrench portion 250 so that the fixture F is turned to be extracted from the alveolar bone, the concave-convex contact surface 225 is closely coupled to an upper side of the fixture F, a friction force effectively works, and thus a fixture F may be rapidly and simply extracted from the alveolar bone while minimizing loss of the alveolar bone.

Here, the concave-convex contact surface 225 formed on the torque transmitting portion 224 may be formed in a variety of shapes such as a square-wave shape or a saw-toothed shape.

FIGS. 24 to 31 are schematic views for describing a method of using an implant fixture remover according to another exemplary embodiment of the present invention.

Figure 24:
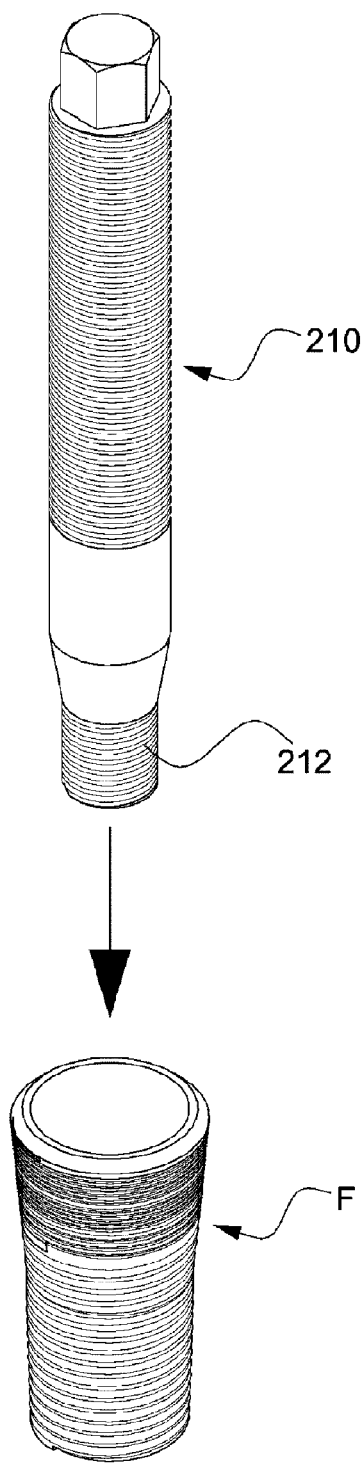
FIGS. 24 to 31 are schematic views for describing a method of using an implant fixture remover according to another exemplary embodiment of the present invention.
Figure 25:
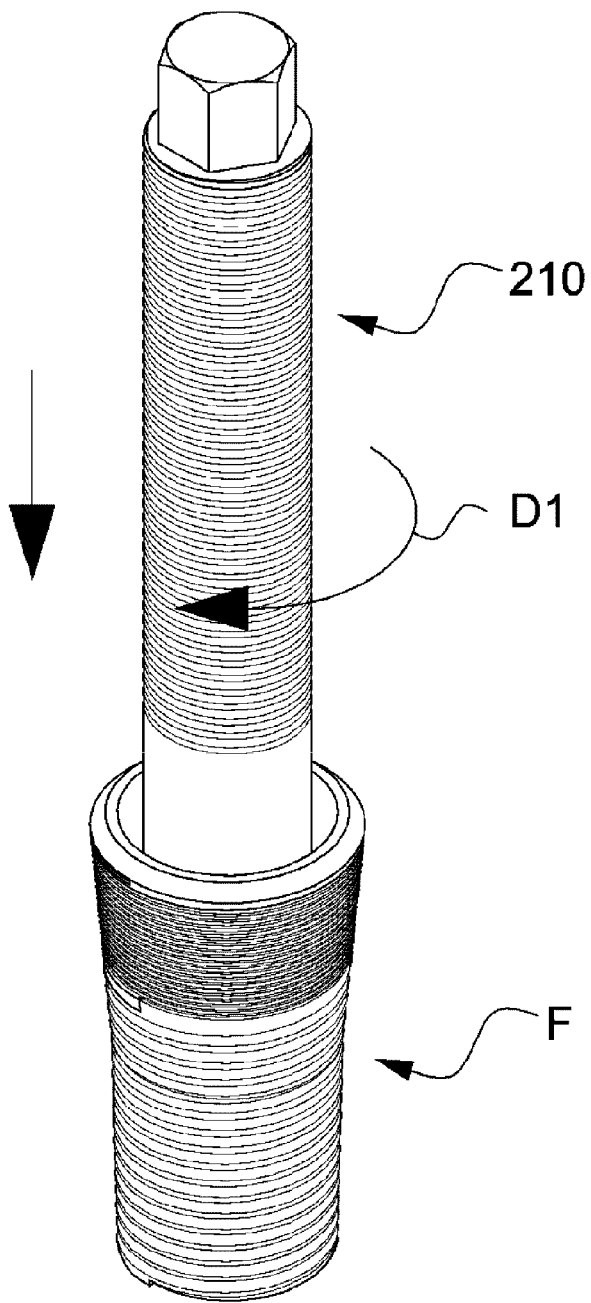

Referring to FIGS. 24 and 25, first, a first thread 212 of a remover screw 210 is screwed to a female screw portion F3 of a fixture F implanted into an alveolar bone.

Here, since the female screw portion F3 and the first thread 212 may be in a direction of a right-handed thread D1, the first thread 212 may be screwed to the female screw portion F3 by turning the remover screw 210 in the direction of the right-handed thread.

Thereafter, a torque transmitting portion 224 and a torque providing portion 222 are temporarily fixed so that a remover driver 220 is slide-inserted into a second thread 214 of the remover screw 210.

Figure 26:
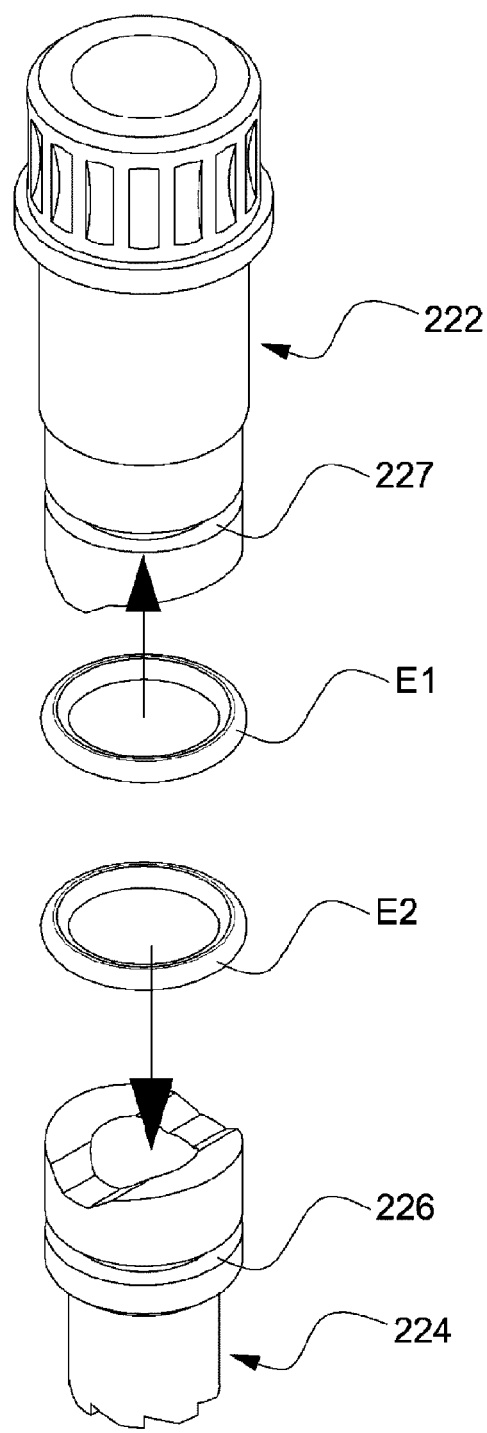
Figure 27:
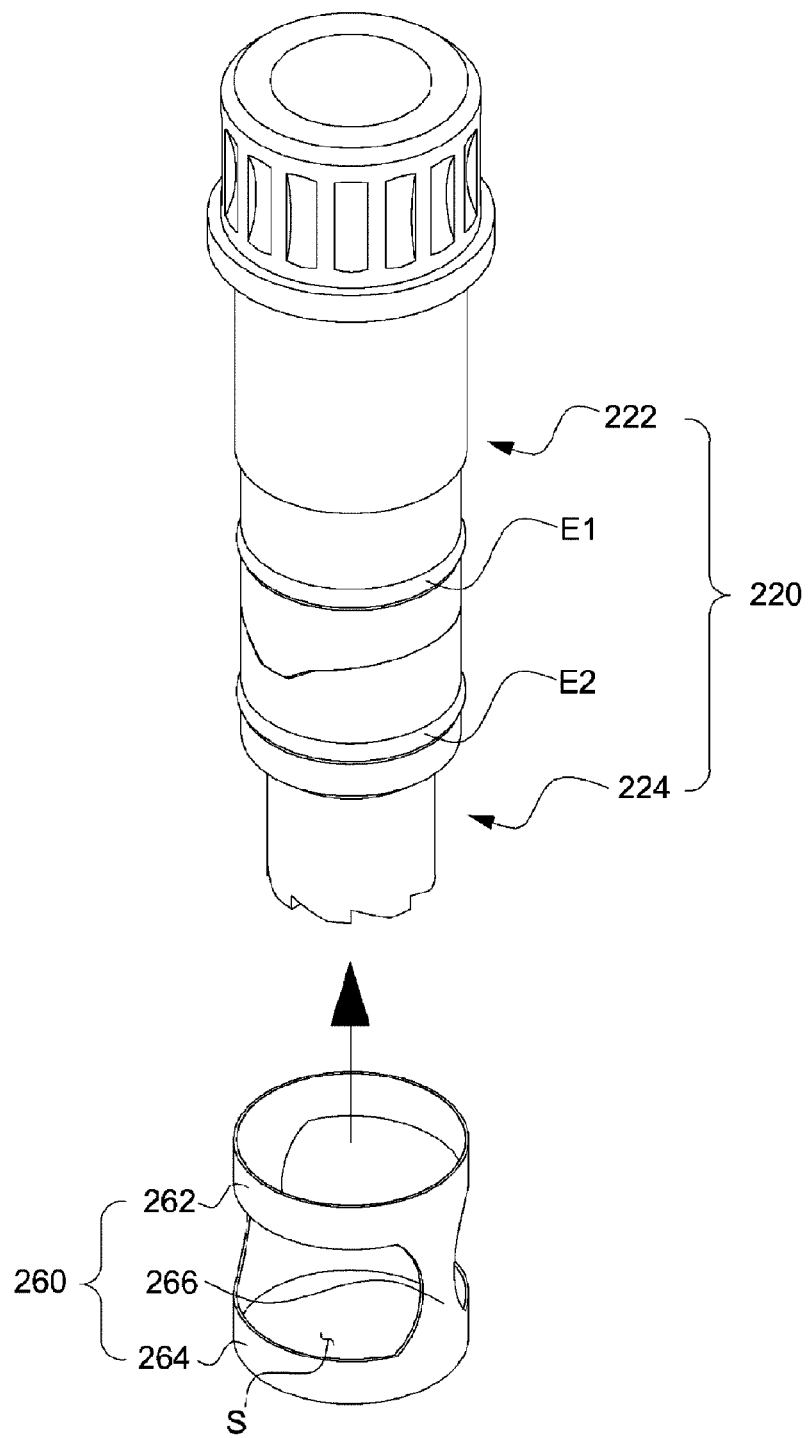

Referring to FIGS. 26 and 27, a first elastic ring E1 is inserted into a first concavity 227 of the torque providing portion 222 of the remover driver 220, and a second elastic ring E2 is inserted into a second concavity 226 of the torque transmitting portion 224.

After the first elastic ring E1 and the second elastic ring E2 are inserted into the first concavity 227 and the second concavity 226, respectively, the torque providing portion 222 and the torque transmitting portion 224 are temporarily fixed by a connection portion 260.

Here, a first close-coupling portion 262 of the connection portion 260 may become in contact with the first elastic ring E1, a second close coupling portion 264 may become in contact with the second elastic ring E2, and it may be determined through a space portion S whether facing surfaces are well aligned.

Figure 28:
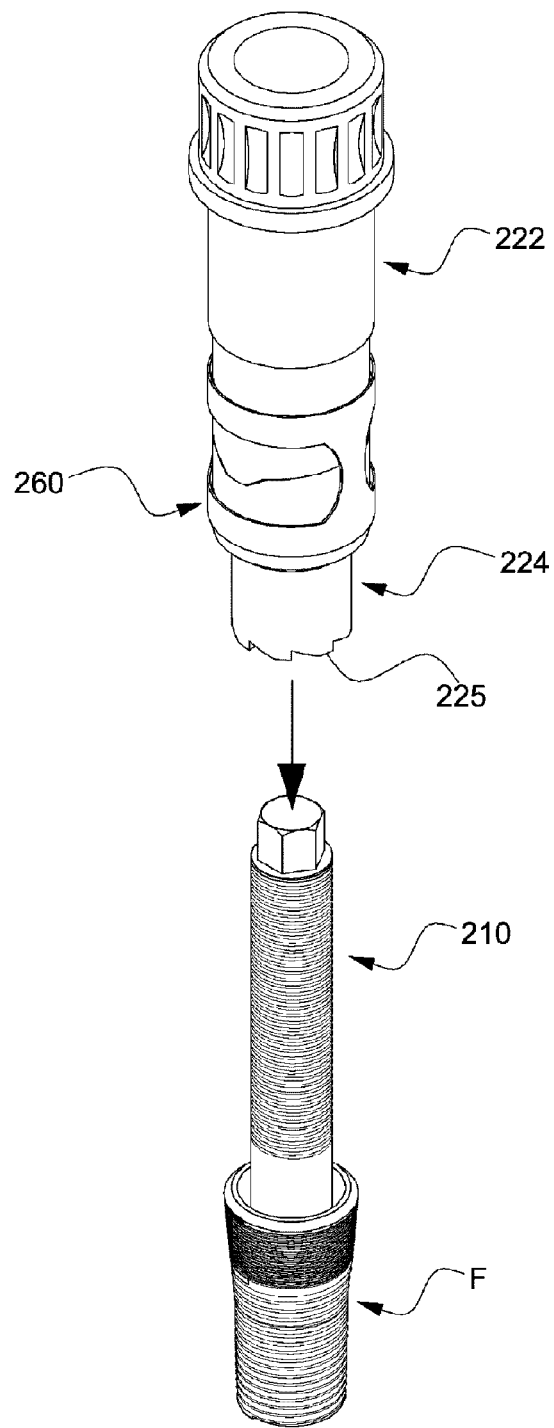
Figure 29:
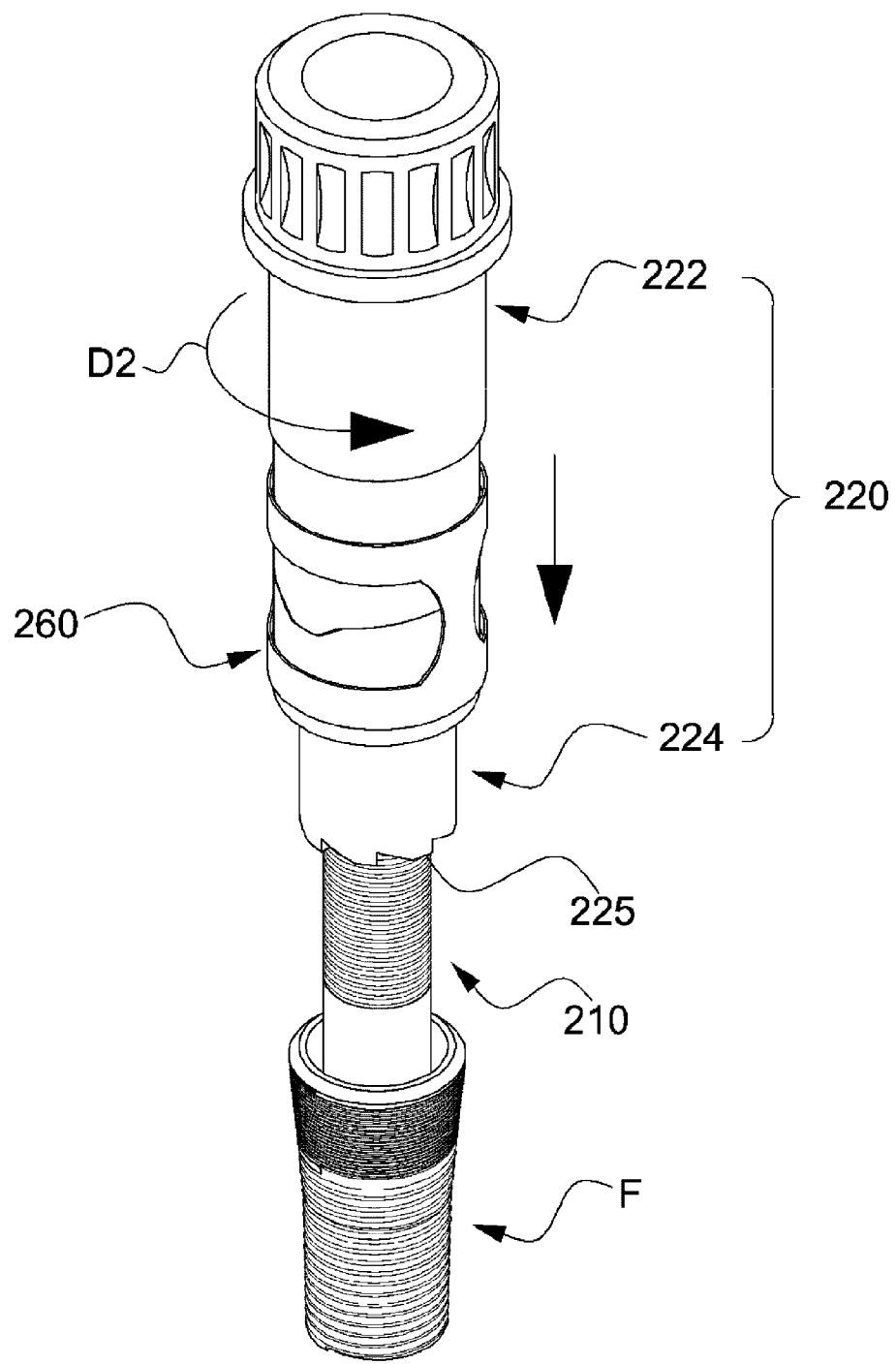

Referring to FIGS. 28 and 29, the remover driver 220 at which the torque providing portion 222 and the torque transmitting portion 224 are temporarily fixed by the connection portion 260 is screwed to the remover screw 210.

As the remover driver 220 is screwed to the remover screw 210, a location of the torque transmitting portion 224 further moves toward an upper end of the fixture F, and the remover driver 220 is turned in a direction of a left-handed thread until a concave-convex contact surface 225 of the torque transmitting portion 224 becomes in contact with the upper end of the fixture F.

When the concave-convex contact surface 225 of the torque transmitting portion 224 becomes in contact with the upper end of the fixture F by turning the remover driver 220 in the direction of the left-handed thread, a coupling of the remover screw 210 and the remover driver 220 to the fixture F is completed. Thereafter, the fixture F is extracted from an alveolar bone.

Figure 30:
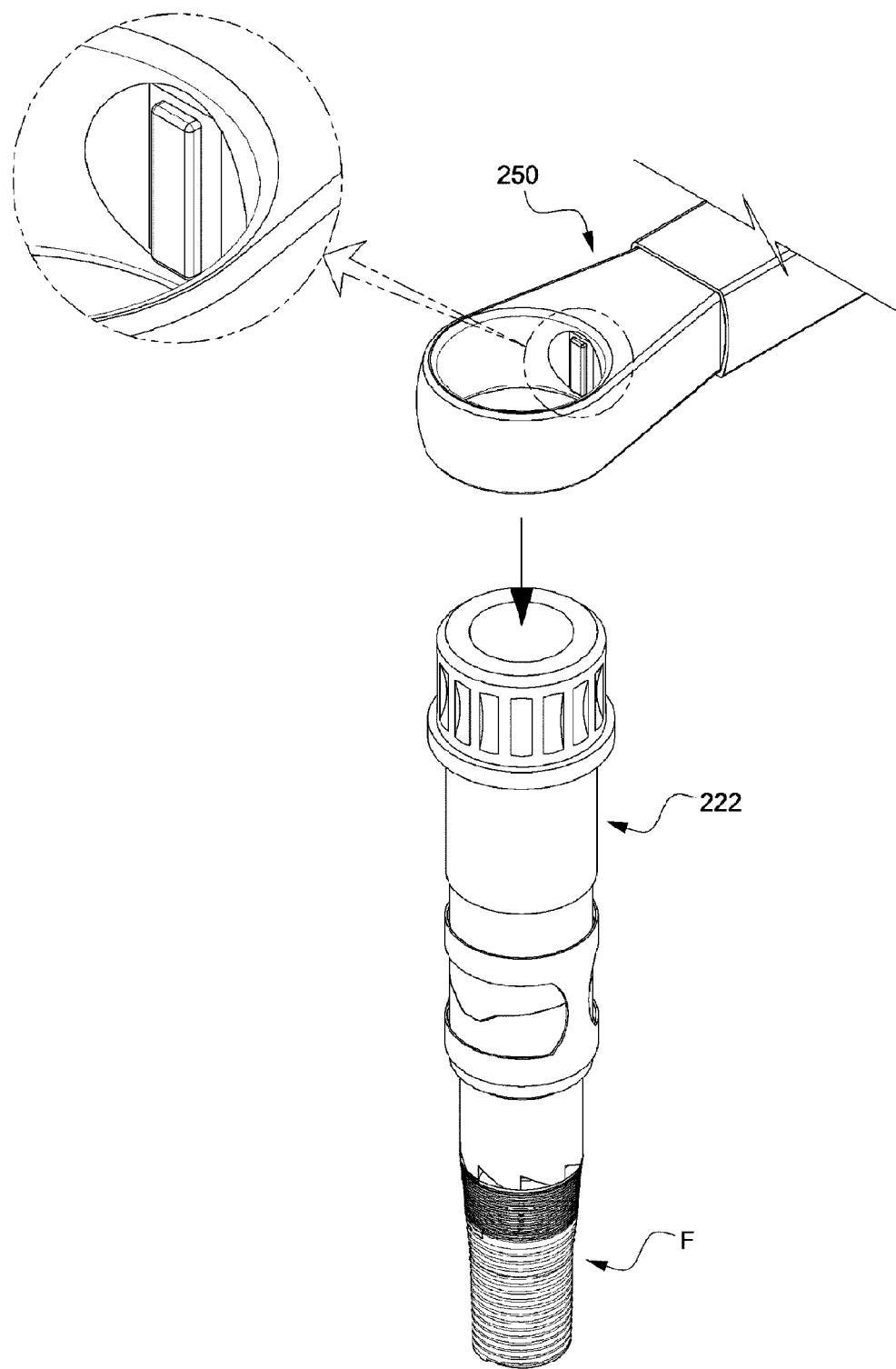
Figure 31:
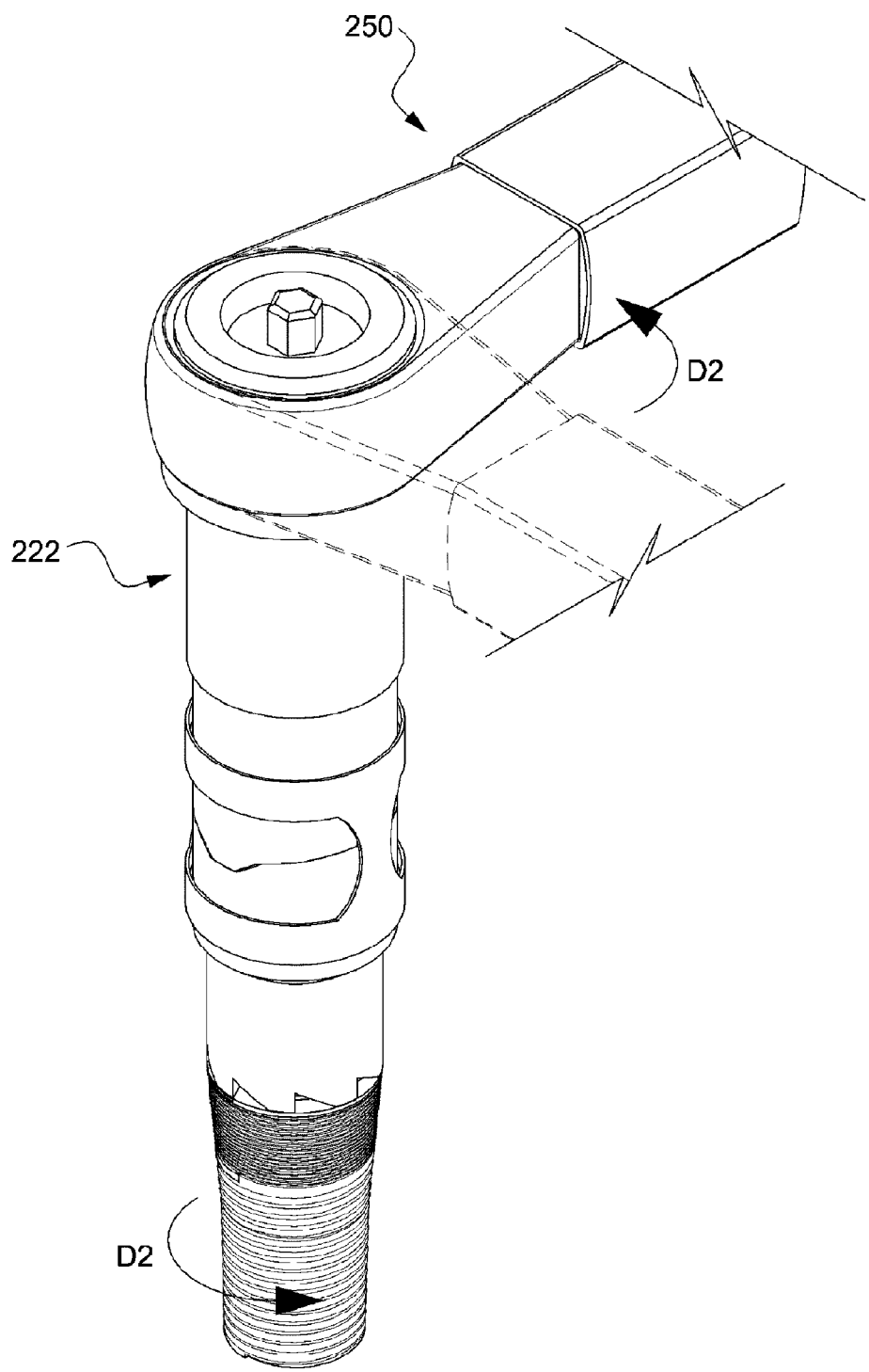

Referring to FIGS. 30 and 31, the torque providing portion 222 may be turned in the direction of the left-handed thread D2 using a wrench portion 250.

Here, the torque transmitting portion 224 receives a pressure applied toward the fixture F at the same time as when the torque transmitting portion 224 is turned by turning the torque providing portion 222 and pressurizes the fixture F while contacting the fixture F and turns the fixture F in the direction of the left-handed thread D2, and thus, the fixture F may be extracted from the alveolar bone.

According to an exemplary embodiment of the present invention, an implant fixture remover may safely separate the fixture from the human bone without removing the surrounding alveolar bone to improve the safety of treatment when a fixture connection portion is damaged with an excessive torque in the course of implanting the fixture and thus may not be inserted or pulled out any more, and which may greatly reduce the time for the treatment.

Further, the implant fixture remover may rapidly and simply extract the fixture from the alveolar bone while minimizing loss of the alveolar bone.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

That is, a specific construction of facing surfaces is not limited the related embodiment and may be applicable to all embodiments.

What is claimed is:

1. An implant fixture remover comprising:
   a remover screw including a first thread formed on one side thereof to be screwed to a female screw portion of an implant fixture implanted into an alveolar bone, and a second thread formed on the other side thereof; and
   a remover driver including a torque transmitting portion slide-inserted onto the remover screw, and a torque providing portion formed to be separated from the torque transmitting portion and directly screwed to the second thread so that the torque transmitting portion maintains direct contact with the fixture,
   wherein a degree of slide insertion of the torque transmitting portion onto the remover screw is determined based on a degree of direct screw coupling of the torque providing portion and the second thread,
   wherein a force, which is applied to facing surfaces of the torque providing portion and the torque transmitting portion by a torque generated by turning the torque providing portion after the torque providing portion is directly screwed to the second thread, is transmitted to the fixture through the torque transmitting portion and works as a repulsive force so that the fixture is extracted from the alveolar bone, and wherein the torque transmitting portion is pressurized toward the fixture in a direct contact state with the fixture.

2. The fixture remover of claim 1, further comprising a connection portion connecting the torque transmitting portion to the torque providing portion so that the torque providing portion is screwed to the second thread and so that the torque transmitting portion and the torque providing portion co-act.

3. The fixture remover of claim 2, wherein the connection portion allows the facing surfaces to be in contact with each other before the torque providing portion is screwed to the second thread.

4. The fixture remover of claim 2, wherein the torque providing portion and the torque transmitting portion respectively comprises a first concavity and a second concavity recessed in a circumferential direction, and further comprises a first elastic ring and a second elastic ring respectively inserted into the first concavity and the second concavity and elastically deformed by contacting the connection portion so that the torque providing portion and the torque transmitting portion are temporarily fixed to coact by the connection portion.

5. The fixture remover of claim 1, wherein a direction of the first thread is formed to be opposite a direction of the second thread.

6. The fixture remover of claim 1, wherein the facing surfaces are defined by at least two normal vectors.

7. The fixture remover of claim 1, wherein the facing surfaces are symmetrically formed based on a virtual plane including a central axis.

8. The fixture remover of claim 7, wherein the facing surfaces comprise:
   a first facing surface having a first slope based on the central axis;
   a second facing surface formed continuously with the first facing surface and having a second slope greater than the first slope; and
   a third facing surface formed continuously with the second facing surface and having a third slope greater than the second slope.

9. The fixture remover of claim 8, wherein the third facing surface is perpendicular to the virtual plane including the central axis.

10. The fixture remover of claim 8, wherein the first facing surface, the second facing surface, and the third facing surface are each provided in a plural number and formed spaced apart from each other.

11. The fixture remover of claim 8, wherein the number of the third facing surfaces is smaller than that of the first facing surface and the second facing surface.

12. The fixture remover of claim 1, wherein the facing surfaces of the torque providing portion and the torque transmitting portion are formed corresponding to each other.

13. The fixture remover of claim 1, wherein the torque transmitting portion includes a concave-convex contact surface in contact with the fixture so that a pressure applied toward the fixture, which is generated by the torque providing portion, is increased.

* * * * *